(12) United States Patent
Tufenkji et al.

(10) Patent No.: US 10,206,906 B2
(45) Date of Patent: Feb. 19, 2019

(54) SYNERGISTIC COMBINATION OF A PHENOLIC-RICH MAPLE SYRUP EXTRACT AND AN ANTIBIOTIC

(71) Applicant: THE ROYAL INSTITUTION FOR THE ADVANCEMENT OF LEARNING/MCGILL UNIVERSITY, Montreal (CA)

(72) Inventors: Nathalie Tufenkji, Laval (CA); Vimal Maisuria, Montreal (CA)

(73) Assignee: THE ROYAL INSTITUTION FOR THE ADVANCEMENT OF LEARNING/MCGILL UNIVERSITY, Montréal (CA)

(*) Notice: Subject to any disclaimer, the term of this patent is extended or adjusted under 35 U.S.C. 154(b) by 305 days.

(21) Appl. No.: 15/159,980

(22) Filed: May 20, 2016

(65) Prior Publication Data

US 2016/0339071 A1 Nov. 24, 2016

Related U.S. Application Data

(60) Provisional application No. 62/165,243, filed on May 22, 2015.

(51) Int. Cl.
*A61K 36/00* (2006.01)
*A61K 31/43* (2006.01)
*A61K 31/496* (2006.01)
*A61K 36/20* (2006.01)

(52) U.S. Cl.
CPC ............ *A61K 31/43* (2013.01); *A61K 31/496* (2013.01); *A61K 36/20* (2013.01)

(58) Field of Classification Search
CPC ...................................................... A61K 36/00
See application file for complete search history.

(56) References Cited

FOREIGN PATENT DOCUMENTS

CA           2658916 A1 *  9/2010  ............ A01G 23/14

OTHER PUBLICATIONS

Bharti, Combination Studies of Oreganum Vulgare Extract Fractions and Volatile Oil along with Ciprofloxacin and Fluconazole against Common Fish Pathogens. Advanced pharmaceutical bulletin, (2013) vol. 3, No. 1, pp. 239-246 (Year: 2013).*
Li et al, Effects of maple (Acer) plant part extracts on proliferation, apoptosis and cell cycle arrest of human tumorigenic and non-tumorigenic colon cells. Phytotherapy research : PTR, (Jul. 2012) vol. 26, No. 7, pp. 995-1002 (Year: 2012).*
Gurtowska et al, Ciprofloxacin criteria in antimicrobial prophylaxis and bladder cancer recurrence. Medical Science Monitor, (2010) vol. 16, No. 10, pp. RA218-RA223 (Year: 2010).*

* cited by examiner

*Primary Examiner* — Qiuwen Mi
(74) *Attorney, Agent, or Firm* — Norton Rose Fulbright Canada

(57) ABSTRACT

It is provided an anti-microbial composition comprising a phenolic-rich extract such as a phenolic-rich maple syrup extract (PRMSE) and at least one antibiotic and a method of treating a bacterial infection comprising administering to a subject in need thereof a phenolic-rich extract and at least one antibiotic.

15 Claims, 10 Drawing Sheets
Specification includes a Sequence Listing.

SYNERGISTIC COMBINATION OF A PHENOLIC-RICH MAPLE SYRUP EXTRACT AND AN ANTIBIOTIC

CROSS-REFERENCE TO RELATED APPLICATIONS

This application claims priority from U.S. Provisional Application Ser. No. 62/165,243, filed May 22, 2015, the entire content of which is incorporated herein by reference.

TECHNICAL FIELD

It is provided an anti-microbial composition comprising a phenolic-rich extract and at least one antibiotic.

BACKGROUND

Gram-negative and Gram-positive bacteria colonize surfaces in health care settings, on indwelling medical devices, and even on live tissue, leading to infections that are often treated with antibiotic therapy. However, two major factors complicate the effectiveness of antibiotic treatments, namely (i) the rising number of antibiotic-resistant bacteria, and (ii) the formation of biofilms. These complications lead to increased patient morbidity, increased costs of treatment, and higher rates of hospitalization.

Antibiotic resistance is the inevitable evolutionary survival mechanism of bacteria which is aggravated by the over-use of antibiotics in the medical and farming industries. Bacterial biofilms are structured, surface-associated microbial communities, protected by a self-produced matrix of extracellular polymeric substances, and are the most common mode of bacterial growth. Formation of biofilms complicates the treatment of infections because bacteria in biofilm mode are generally very persistent, requiring considerably higher doses of antibiotics for treatment compared to planktonic bacteria. High antibiotic doses disturb the body's microbiome, putting the patient's health at risk, as well as increasing the potential for development of antibiotic-resistant strains.

In view of the reduced effectiveness of current therapies and a declining repertoire of clinically useful drugs, there is a need to be provided with molecules endowed with anti-microbial and/or anti-biofilm properties.

SUMMARY

It is provided anti-microbial composition comprising a phenolic-rich extract and at least one antibiotic.

In an embodiment, the phenolic-rich extract is a phenolic-rich maple syrup extract (PRMSE).

In a further embodiment, the at least one antibiotic is a fluoroquinolone antibiotic, a β-lactam antibiotic, aminoglycoside, polyketides, glycopeptides, benzenoids, macrolides, ansamycins, sulfonamides, chloramphenicol, oxazolidinones, carboxylic acids antibiotic, organic phosphonic acids antibiotic, quinolones and their derivatives.

In another embodiment, the at least one antibiotic is at least one of ciprofloxacin, carbenicillin, ampicillin, penicillin, kanamycin, gentamycin, tetracycline, levofloxacin, trimethoprim, sulfamethoxazole, norfloxacin, nitrofurantoin, fosfomycin, azithromycin, minocycline, am ikacin, cephalosporin, erythromycin, daptomycin, vancomycin and their derivatives.

In an additional embodiment, the PRMSE is from *Acer nigrum*, *Acer lanum*, *Acer acuminatum*, *Acer albopurpurascens*, *Acer argutum*, *Acer barbinerve*, *Acer buergerianum*, *Acer caesium*, *Acer campbellii*, *Acer campestre*, *Acer capillipes*, *Acer cappadocicum*, *Acer carpinifolium*, *Acer caudatifolium*, *Acer caudatum*, *Acer cinnamomifolium*, *Acer circinaturn*, *Acer cissifolium*, *Acer crassum*, *Acer crataegifolium*, *Acer davidii*, *Acer decandrum*, *Acer diabolicum*, *Acer distylum*, *Acer divergens*, *Acer erianthum*, *Acer erythranthum*, *Acer fabri*, *Acer garrettii*, *Acer glabrum*, *Acer grandidentatum*, *Acer griseum*, *Acer heldreichii*, *Acer henryi*, *Acer hyrcanum*, *Acer ibericum*, *Acer japonicum*, *Acer kungshanense*, *Acer kweilinense*, *Acer laevigatum*, *Acer laurinum*, *Acer lobelii*, *Acer lucidum*, *Acer macrophyllum*, *Acer mandshuricum*, *Acer maximowiczianum*, *Acer miaoshanicum*, *Acer micranthum*, *Acer miyabei*, *Acer mono*, *Acer monox*, *Acer truncatum*, *Acer monspessulanum*, *Acer negundo*, *Acer ningpoense*, *Acer nipponicum*, *Acer oblongum*, *Acer obtusifolium*, *Acer oliverianum*, *Acer opalus*, *Acer palmatum*, *Acer paxii*, *Acer pectinatum*, *Acer pensylvanicum*, *Acer pentaphyllum*, *Acer pentapomicum*, *Acer pictum*, *Acer pilosum*, *Acer platanoides*, *Acer poliophyllum*, *Acer pseudoplatanus*, *Acer pseudosieboldianum*, *Acer pubinerve*, *Acer pycnanthum*, *Acer rubrum*, *Acer rufinerve*, *Acer saccharinum*, *Acer saccharum*, *Acer sempervirens*, *Acer shirasawanum*, *Acer sieboldianum*, *Acer sinopurpurescens*, *Acer spicatum*, *Acer stachyophyllum*, *Acer sterculiaceum*, *Acer takesimense*, *Acer tataricum*, *Acer tegmentosum*, *Acer tenuifolium*, *Acer tetramerum*, *Acer trautvetteri*, *Acer triflorum*, *Acer truncatum*, *Acer tschonoskii*, *Acer turcomanicum*, *Acer ukurunduense*, *Acer velutinum*, *Acer wardii*, *Acer×peronai*, or *Acer×pseudoheldreichii*.

In an embodiment, the composition reduces biofilm formation of a bacterial strain.

In a further embodiment, the anti-microbial composition is against Gram-negative or Gram-positive bacteria.

In another embodiment, the anti-microbial composition is against a bacterial strain of *Escherichia coli*, *Proteus mirabilis*, *Pseudomonas aeruginosa*, *Salmonella* species, *Enterobacter cloacae*, *Burkholderia cepacia*, *Chromobacterium violaceum*, *Klebsiella pneumoniae*, *Helicobacter pylori*, *Acinetobacter baumannii*, *Vibrio cholera*, *Mycoplasma pneumoniae*, *Neisseria gonorrhoeae*, *Legionella pneumophila*, *Serratia* species, *Shigella* species, *Rickettsia rickettsia*, *Chlamydia pneumoniae*, *Mycobacterium tuberculosis*, *Yersinia* species, *Moraxella catarrhalis* or *Proteobacteria* pathogens.

In another embodiment, the extract comprises a catechol a catechaldehyde, a gallic acid, a syringaldehyde, a vanillin, and/or a hydroxybenzoic acid.

In an additional embodiment, the extract inhibits the efflux pump of a bacterium.

In an embodiment, the composition represses the expression of a gene associated with multiple drug resistance, motility, virulence determinants, adhesion and/or biofilm formation.

In another embodiment, the gene associated with multiple drug resistance is emrA, acrB, marC, acrA, oprM, mexA or mexX; the gene associated with motility is fliC, flhD, motB, fimH, fimA, papA2, flaA, fleQ; the gene associated with virulence determinants is chuA, cysJ, plcH, phzS or pvdA; the gene associated with adhesion is fimH, fimA, papA2, atfB, cupA1 or pelA; and the gene associated with biofilm formation is uvrY, ureD or lasB.

It is also provided a method of treating a bacterial infection comprising administering to a subject in need thereof a phenolic-rich extract as defined herein and at least one antibiotic.

In an embodiment, the subject is a human, an animal, a *Galleria mellonella* or a *Drosophila melanogaster*.

In a further embodiment, the composition described herein is used for treating an urinary tract infection, lung infection, kidney infection, gastrointestinal infection, wound infection, acute sinusitis, skin and skin structure infections, bone and joint infections, lyme disease, typhus fever, rocky mountain spotted fever, rickettsialpox, or tuberculosis.

BRIEF DESCRIPTION OF THE DRAWINGS

Reference will now be made to the accompanying drawings.

In FIG. 13A and FIG. 13B, LasA: staphylolytic protease and AprA: alkaline protease. Results are expressed as means and standard deviations (SD) of triplicate assays (*p<0.05). In FIG. 13C, total proteolytic activity is determined on skim milk agar plate.

DETAILED DESCRIPTION

Figure 1:
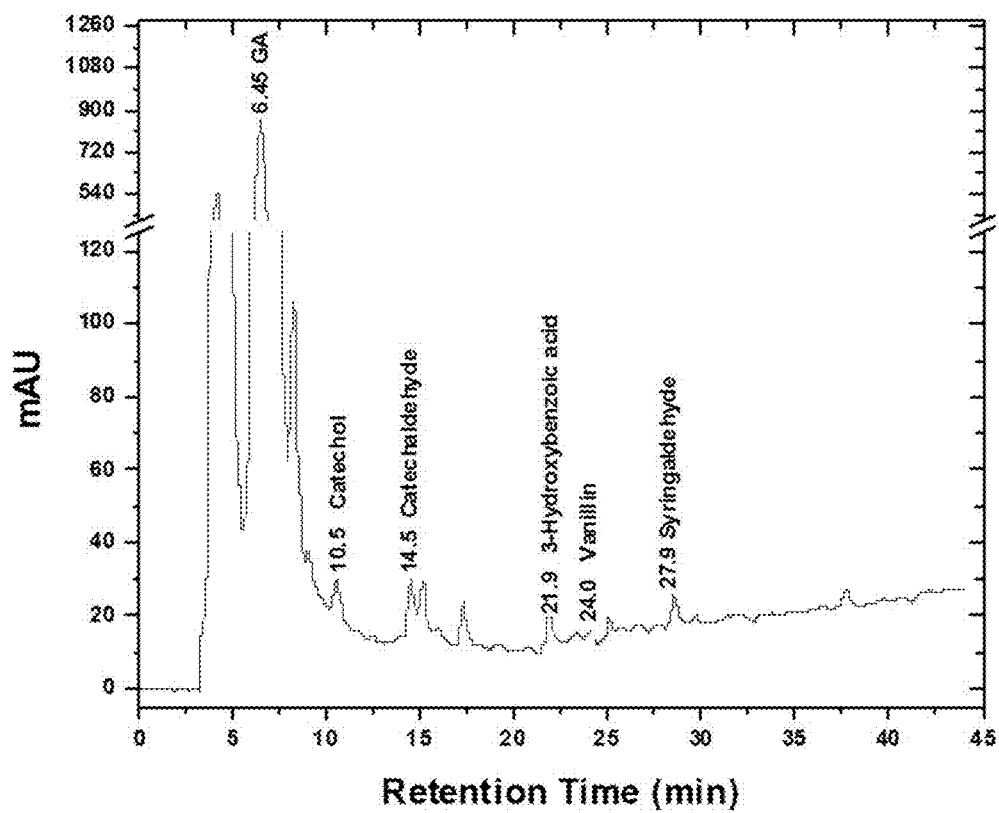
FIG. 1 illustrates HPLC-UV chromatograms of polyphenolic-rich maple syrup extract (PRMSE). Compounds were identified based on the peaks obtained from pure phenolic compounds in separate runs. The numbers on the peaks correspond to the retention time of pure phenolic compounds (GA: gallic acid).

In accordance with the present disclosure, there is provided anti-microbial composition comprising a phenolic-rich extract and at least one antibiotic.

As encompassed herein the phenolic-rich extract is preferably a phenolic-rich maple syrup extract (PRMSE).

Many plants synthesize aromatic substances, most of which are phenols or their oxygen-substituted derivatives. These phenolic compounds are believed to be promising candidates as complementary therapeutics since they can modify bacterial behavior by affecting bacterial motility, surface adhesion, biofilm formation, quorum sensing, and production of virulence determinants. Traditional medicinal approaches owe their significance to the bioactive components that have their origin in plant sources and many are associated with routine dietary habits.

Syrup obtained by concentrating the sap from certain maple species of North American maple trees (i.e., the sugar maple, such as for example *Acer saccharum* Marsh, and the red maple, *A. rubrum* L.), contains a vast number of natural and process-derived phytochemicals, the majority of which are phenolic compounds. Phenolic-Rich Maple Syrup Extracts (PRMSE) are obtained by extracting the phenolic compounds of maple syrup with organic solvents. These extracts have been reported to exhibit anti-proliferative effects against a panel of human tumor cell lines.

Encompassed herein is a maple tree of a species such as *Acer nigrum, Acer lanum, Acer acuminatum, Acer albopurpurascens, Acer argutum, Acer barbinerve, Acer buergerianum, Acer caesium, Acer campbellii, Acer campestre, Acer capillipes, Acer cappadocicum, Acer carpinifolium, Acer caudatifolium, Acer caudatum, Acer cinnamomifolium, Acer circinaturn, Acer cissifolium, Acer crassum, Acer crataegifolium, Acer davidii, Acer decandrum, Acer diabolicum, Acer distylum, Acer divergens, Acer erianthum, Acer erythranthum, Acer fabri, Acer garrettii, Acer glabrum, Acer grandidentatum, Acer griseum, Acer heldreichii, Acer henryi, Acer hyrcanum, Acer ibericum, Acer japonicum, Acer kungshanense, Acer kweilinense, Acer laevigatum, Acer laurinum, Acer lobelii, Acer lucidum, Acer macrophyllum, Acer mandshuricum, Acer maximowiczianum, Acer miaoshanicum, Acer micranthum, Acer miyabei, Acer mono, Acer monox, Acer truncatum, Acer monspessulanum, Acer negundo, Acer ningpoense, Acer nipponicum, Acer oblongum, Acer obtusifolium, Acer oliverianum, Acer opalus, Acer palmatum, Acer paxii, Acer pectinatum, Acer pensylvanicum, Acer pentaphyllum, Acer pentapomicum, Acer pictum, Acer pilosum, Acer platanoides, Acer poliophyllum, Acer pseudoplatanus, Acer pseudosieboldianum, Acer pubinerve, Acer pycnanthum, Acer rubrum, Acer rufinerve, Acer saccharinum, Acer saccharum, Acer sempervirens, Acer shirasawanum, Acer sieboldianum, Acer sinopurpurescens, Acer spicatum, Acer stachyophyllum, Acer sterculiaceum, Acer takesimense, Acer tataricum, Acer tegmentosum, Acer tenuifolium, Acer tetramerum, Acer trautvetteri, Acer triflorum, Acer truncatum, Acer tschonoskii, Acer turcomanicum, Acer ukurunduense, Acer velutinum, Acer wardii, Acer× peronai,* or *Acer× pseudoheldreichii.*

Herein, it is provided the anti-bacterial efficacy of phenolic-rich maple syrup extract (PRMSE) in treating clinical and multiple drug-resistant pathogenic bacterial strains. Experiments disclosed herein involve combinations of phenolic rich maple syrup extract and at least one antibiotic (ciprofloxacin or carbenicillin) at different concentrations analyzed for growth inhibition of each pathogenic bacterial strain (*Escherichia coli* CFT073, *Proteus mirabilis* HI4320, *Pseudomonas aeruginosa* PAO1 and *P. aeruginosa* PA14).

The extract described herein can be effective composition against a bacterial strain of *Escherichia coli, Proteus mirabilis, Pseudomonas aeruginosa, Salmonella* species, *Enterobacter cloacae, Burkholderia cepacia, Chromobacterium violaceum, Klebsiella pneumoniae, Helicobacter pylori, Acinetobacter baumannii, Vibrio cholera, Mycoplasma pneumoniae, Neisseria gonorrhoeae, Legionella pneumophila, Serratia* species, *Shigella* species, *Rickettsia rickettsia, Chlamydia pneumoniae, Mycobacterium tuberculosis, Yersinia* species, *Moraxella catarrhalis* or *Proteobacteria* pathogens.

Another set of experiments demonstrating anti-biofilm activity of PRMSE against pathogenic bacterial strains is disclosed. The anti-bacterial properties of PRMSE increase antibiotic susceptibility of each pathogenic bacterial strain at sub-inhibitory concentrations. This extract also significantly reduced biofilm formation and eradication of monoculture biofilm of each pathogenic bacterial strain from the surface of silicone discs at sub-lethal concentrations. Transcriptome analysis revealed that PRMSE significantly repressed the expression of multiple drug resistance genes, motility and attachment-related genes, and virulence-associated genes of pathogenic clinical strains. Two key components of PRMSE, namely, gallic acid and catechol, were found to increase outer-membrane permeability, and PRMSE effectively inhibited efflux pumps involved in multidrug resistance in pathogenic bacteria.

As encompassed herein, the antibiotic used in combination with the extract described herein can be a fluoroquinolone antibiotic, a β-lactam antibiotic, am inoglycoside, polyketides, glycopeptides, benzenoids, macrolides, ansamycins, sulfonamides, chloramphenicol, oxazolidinones, carboxylic acids antibiotic, organic phosphonic acids antibiotic, quinolones and their derivatives.

Alternatively, the antibiotic encompassed herein can be antibiotic ciprofloxacin, carbenicillin, ampicillin, penicillin, kanamycin, gentamycin, tetracycline, levofloxacin, trimethoprim, sulfamethoxazole, norfloxacin, nitrofurantoin, fosfomycin, azithromycin, minocycline, am ikacin, cephalosporin, erythromycin, daptomycin, vancomycin and their derivatives.

HPLC chromatograms (FIG. 1) show the presence of six predominant phenolic compounds in PRMSE: gallic acid, 1,2-dihydroxybenzene (catechol), 3,4-dihydroxybenzaldehyde (catechaldehyde), syringaldehyde, vanillin and 3-hydroxybenzoic acid. Based on their bioactive properties reported in the literature, the following four compounds were selected, purchased in pure form and screened along with PRMSE for growth inhibition and synergy with ciprofloxacin: gallic acid, catechol, catechaldehyde, and syringaldehyde.

MICs for PRMSE and ciprofloxacin against the bacterial strains *E. coli* CFT073, *P. mirabilis* HI4320, *P. aeruginosa* PAO1 and *P. aeruginosa* PA14 are shown in Table 1.

TABLE 1

Synergistic interactions of ciprofloxacin and PRMSE for growth inhibition

| Interactions | Bacterial strains | | | |
|---|---|---|---|---|
| | E. coli CFT073 | P. mirabilis HI4320 | P. aeruginosa PAO1 | P. aeruginosa PA14 |
| MIC of ciprofloxacin ($\mu g\ mL^{-1}$) | 0.008 | 0.016 | 1.0 | 0.06 |
| $FIC^a$ of ciprofloxacin | 0.25 | 0.02 | 0.03 | 0.03 |
| MIC of PRMSE ($mg\ mL^{-1}$) | 25 | 50 | 50 | 50 |
| $FIC^a$ of PRMSE | 0.13 | 0.13 | 0.06 | 0.06 |
| $FICI^b$ | 0.38 | 0.14 | 0.1 | 0.1 |
| Synergistic? | Yes | Yes | Yes | Yes |

$^a$FIC: Fractional Inhibitory Concentration, FIC = MIC of compound 1 in the combination, divided by the MIC of compound 1 alone
$^b$FICI: Fractional Inhibitory Concentration Index, FICI = $FIC_{compound\ 1}$ + $FIC_{compound\ 2}$ To investigate the presence of synergistic interaction between ciprofloxacin (a fluoroquinolone, which has biofilm penetration properties) and PRMSE, a checkerboard microdilution analysis was performed. The corresponding functional inhibitory concentration index (FICI) values were <0.5 for all tested strains (Table 1), demonstrating a strong synergistic effect between PRMSE and ciprofloxacin. Because P. aeruginosa is known to be partially resistant to carbenicillin (a β-lactam antibiotic), the effect of PRMSE on the susceptibility of the P. aeruginosa strains towards carbenicillin was also investigated. The MIC and FICI values in Table 2 show that PRMSE acted in synergy with carbenicillin against the growth of the two P. aeruginosa strains.

TABLE 2

Synergistic interactions of carbenicillin and PRMSE for growth inhibition

| Interactions | P. aeruginosa strains | |
|---|---|---|
| | PAO1 | PA14 |
| MIC of carbenicillin ($\mu g\ mL^{-1}$) | 64 | 128 |
| FIC of carbenicillin | 0.13 | 0.063 |
| MIC of PRMSE ($mg\ mL^{-1}$) | 50 | 50 |
| FIC of PRMSE | 0.03 | 0.063 |
| FICI | 0.16 | 0.13 |
| Synergistic? | Yes | Yes |

The MICs for the pure phenolic compounds are presented in Table 3.

TABLE 3

Interaction of phenolic constituents of PRMSE with ciprofloxacin

| Bacterial Strains | Constituents | MIC ($mg\ mL^{-1}$) | Interactions | | |
|---|---|---|---|---|---|
| | | | $FIC^a$ of ciprofloxacin | FIC of compound | FICI |
| E. coli CFT073 | gallic acid | 5 | 1 | 1 | 2 |
| | catechol | 1.25 | 0.25 | 0.25 | 0.5* |
| | catechaldehyde | 1.25 | 1 | 1 | 2 |
| | syringaldehyde | 5 | 0.5 | 0.25 | 0.75 |
| P. mirabilis HI4320 | gallic acid | 5 | 1 | 1 | 2 |
| | catechol | 1.25 | 0.25 | 0.25 | 0.5* |
| | catechaldehyde | 1.25 | 0.5 | 1 | 1.5 |
| | syringaldehyde | 5 | 0.5 | 0.5 | 1 |
| P. aeruginosa PAO1 | gallic acid | 5 | 1 | 1 | 2 |
| | catechol | 2.5 | 0.25 | 0.25 | 0.5* |
| | catechaldehyde | 1.25 | 0.5 | 0.51 | 1.01 |
| | syringaldehyde | 5 | 1 | 1 | 2 |
| P. aeruginosa PA14 | gallic acid | 5 | 1 | 1 | 2 |
| | catechol | 2.5 | 0.25 | 0.25 | 0.5* |
| | catechaldehyde | 1.25 | 1 | 1 | 2 |
| | syringaldehyde | 5 | 0.5 | 0.25 | 0.75 |

*Values represent synergistic interaction
$^a$FIC: Fractional Inhibitory Concentration, FIC = MIC of compound 1 in the combination, divided by the MIC of compound 1 alone
$^b$FICI: Fractional Inhibitory Concentration Index, FICI = $FIC_{compound\ 1}$ + $FIC_{compound\ 2}$.

Amongst the four selected phenolic constituents of PRMSE, catechol (at 1.25 mg mL$^{-1}$ for both E. coli CFT073 and P. mirabilis HI4320, and at 2.5 mg mL$^{-1}$ for P. aeruginosa PAO1 and PA14) and catechaldehyde (at 1.25 mg mL$^{-1}$ for all four strains) were found to clearly inhibit growth at lower concentrations. Furthermore, interaction of these four phenolic compounds with ciprofloxacin was examined using a checkerboard microdilution assay. The results presented in Table 3 show that the combination of catechol and ciprofloxacin was the only synergistic combination (<0.5 FICI) for all investigated strains.

To investigate possible synergistic antimicrobial action among the four phenolic constituents of PRMSE, different combinations of gallic acid, catechol, catechaldehyde and syringaldehyde were tested using the checkerboard microdilution assay; the corresponding FICIs are presented in Table 4.

TABLE 4

Interaction of individual phenolic constituents of PRMSE.

| Bacterial strains | Phenolic constituents | $FIC^a$ | | | $FICI^b$ | | |
|---|---|---|---|---|---|---|---|
| | | gallic acid | catechol | catechaldehyde | gallic acid | catechol | catechaldehyde |
| E. coli CFT073 | catechol | 0.13 | $NA^c$ | — | 0.25* | NA | — |
| | catechaldehyde | 0.25 | 0.25 | NA | 0.5* | 0.5* | NA |
| | syringaldehyde | 0.5 | 0.25 | 0.25 | 0.75 | 0.31* | 0.31* |
| P. mirabilis HI4320 | catechol | 0.13 | NA | — | 0.37* | NA | — |
| | catechaldehyde | 0.13 | 0.25 | NA | 0.37* | 0.5* | NA |
| | syringaldehyde | 0.5 | 0.25 | 0.25 | 1 | 0.75 | 0.75 |
| P. aeruginosa PAO1 | catechol | 0.25 | NA | — | 0.5* | NA | — |
| | catechaldehyde | 0.13 | 0.25 | NA | 0.37* | 0.37* | NA |
| | syringaldehyde | 0.5 | 0.25 | 0.25 | 1 | 0.5* | 0.5* |

TABLE 4-continued

Interaction of individual phenolic constituents of PRMSE.

| Bacterial strains | Phenolic constituents | FIC[a] | | | FICI[b] | | |
|---|---|---|---|---|---|---|---|
| | | gallic acid | catechol | catechaldehyde | gallic acid | catechol | catechaldehyde |
| P. aeruginosa PA14 | catechol | 0.25 | NA | — | 0.37* | NA | — |
| | catechaldehyde | 0.25 | 0.25 | NA | 0.5* | 0.5* | NA |
| | syringaldehyde | 0.13 | 0.5 | 0.5 | 0.63 | 1 | 1 |

*Values represent synergistic interaction
[a]FIC: Fractional Inhibitory Concentration, FIC = MIC of compound 1 in the combination, divided by the MIC of compound 1 alone.
[b]FICI: Fractional Inhibitory Concentration Index, FICI = FIC$_{compound\ 1}$ + FIC$_{compound\ 2}$
[c]NA: not applicable The most potent synergy on growth inhibition was observed for gallic acid-catechol and gallic acid-catechaldehyde pairs, resulting in FICIs of 0.25-0.50, whereas all combinations of gallic acid with syringaldehyde led to FICIs ranging between 0.63-1.0 (Table 4), indicating no synergistic interaction. Interestingly, catechol exhibited strong synergy for growth inhibition with catechaldehyde against all chosen strains and with syringaldehyde against E. coli CFT073 and P. aeruginosa PAO1, as confirmed by FICIs (Table 4), suggesting that catechol is a potent component of PRMSE, mainly responsible for its antimicrobial activity.

To investigate the potential of PRMSE for biofilm inhibition, biofilms were developed in polystyrene microtitre plates in the presence of different combinations of PRMSE, with and without ciprofloxacin at sub-lethal concentrations. These sub-lethal concentrations of PRMSE 3.13 and 6.25 mg mL$^{-1}$ for E. coli CFT073; 6.25 and 12.5 mg mL$^{-1}$ for P. mirabilis HI4320, P. aeruginosa PAO1 and PA14) and ciprofloxacin (0.0005-0.004 µg mL$^{-1}$ for E. coli CFT073, 0.001-0.008 µg mL$^{-1}$ for P. mirabilis HI4320, 0.00625-0.5 µg mL$^{-1}$ for P. aeruginosa PAO1 and 0.004-0.03 µg mL$^{-1}$ for P. aeruginosa PA14) were chosen for biofilm studies, based on results obtained in the MIC assay. Anti-biofilm activity of PRMSE is presented in FIG. 2; the amount of sessile biomass (OD$_{570}$) was normalized to the level of planktonic growth (OD$_{600}$) to minimize bias from possible differences in growth levels on biofilm quantification. PRMSE alone showed significant inhibition of monoculture biofilm formation of all tested strains (p<0.05). PRMSE in combination with ciprofloxacin (at sub-lethal concentrations) had significant inhibitory effects on biofilm formation (p<0.05) for E. coli CFT073 (~70% inhibition at 6.25 mg mL$^{-1}$), P. mirabilis HI4320 (70% inhibition at 12.5 mg mL$^{-1}$), P. aeruginosa PAO1 (83% inhibition at 12.5 mg mL$^{-1}$) and P. aeruginosa PA14 (~54% inhibition at 12.5 mg mL$^{-1}$), in a dose-dependent manner. Since catechol was the only compound that exhibited synergy in antimicrobial activity with ciprofloxacin (Table 3), only the combination of catechol and ciprofloxacin was analyzed in this assay.

Figure 3:
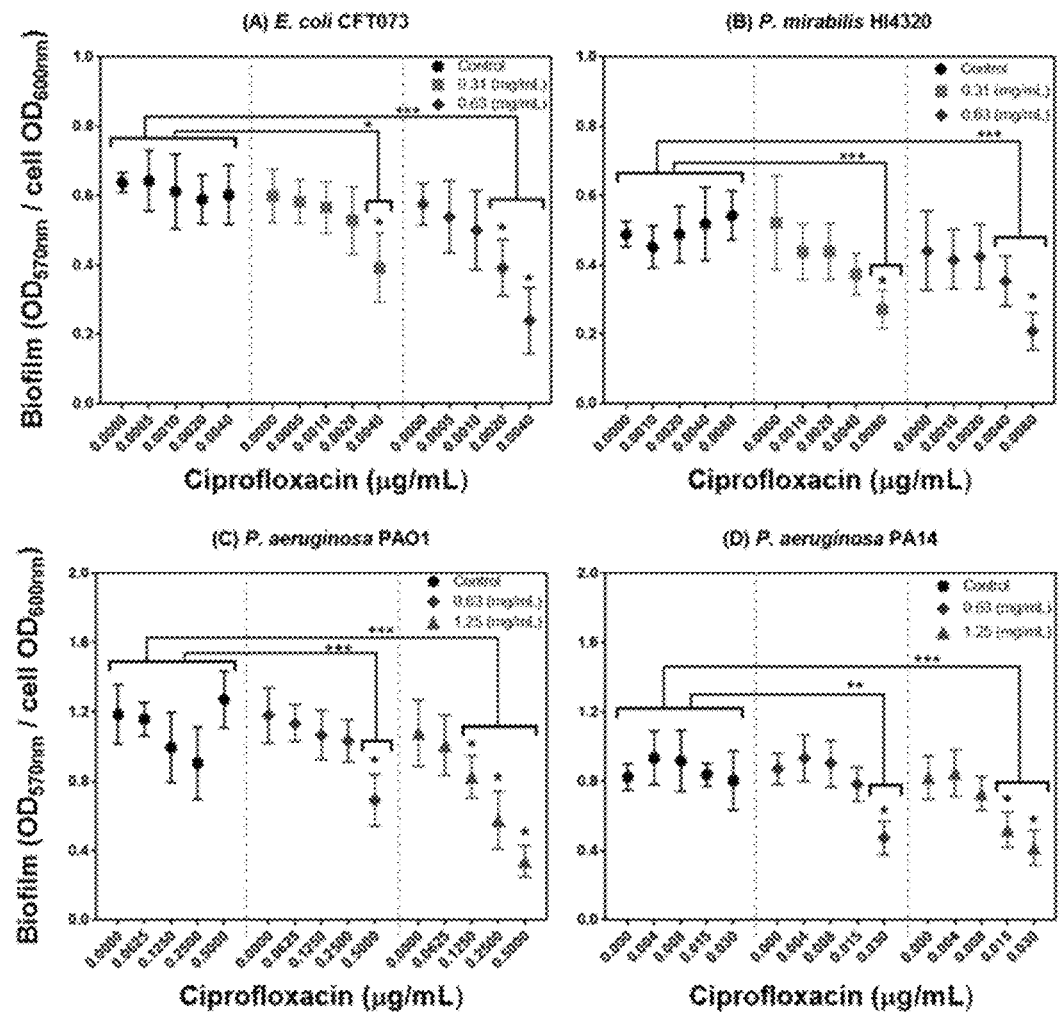
FIG. 3 illustrates the effect of catechol, with and without ciprofloxacin, on biofilm formation of (FIG. 3A) *E. coli* CFT073, (FIG. 3B) *P. mirabilis* HI4320, (FIG. 3C) *P. aeruginosa* PAO1 and (FIG. 3D) *P. aeruginosa* PA14. The graph shows the normalized biofilm level ($OD_{570}$ nm/$OD_{600}$ nm) versus different sub-inhibitory concentrations of ciprofloxacin for each strain grown in LB medium (Control) or in LB medium amended with sub-inhibitory concentrations (0.31, 0.63 and 1.25 mg $mL^{-1}$) of catechol.

Catechol with and without ciprofloxacin (both at sub-lethal concentrations) manifested significant inhibitory effects (p<0.05) on biofilm formation for all four tested strains (FIG. 3).

Figure 4:
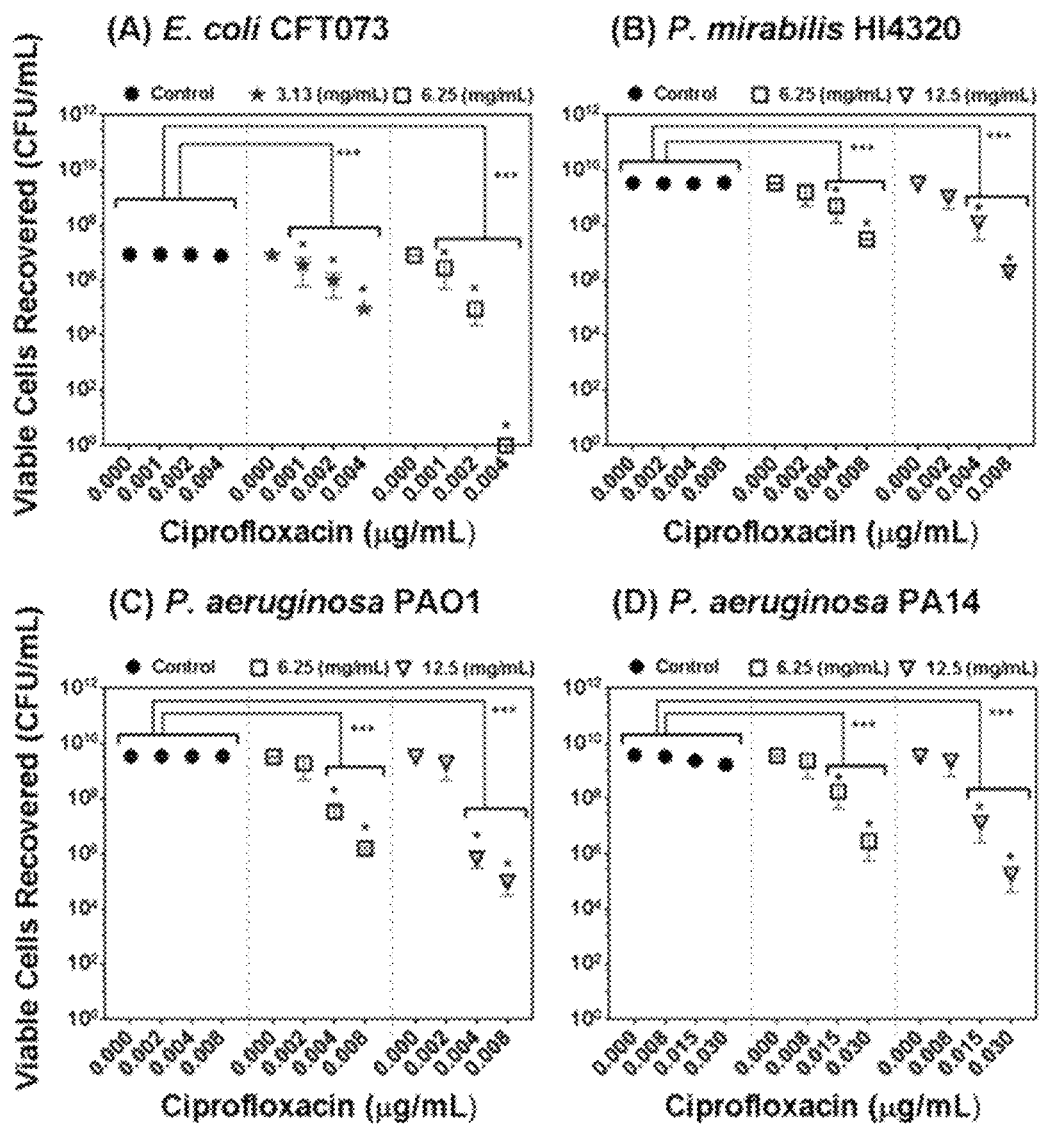
FIG. 4 illustrates the effect of PRMSE, with and without ciprofloxacin, on eradication of monoculture biofilms on silicone discs of (FIG. 4A) *E. coli* CFT073, (FIG. 4B) *P. mirabilis* HI4320, (FIG. 4C) *P. aeruginosa* PAO1 and (D) *P. aeruginosa* PA14. The graph presents recovered bacterial cells from biofilm on silicone discs versus different sub-inhibitory concentrations of ciprofloxacin for each strain exposed to PBS (Control) or in PBS amended with sub-inhibitory concentrations of PRMSE (3.13, 625 and 12.5 mg $mL^{-1}$).

To analyze the applicability of PRMSE to eradicate biofilm from biomaterial surfaces, an in vitro biofilm assay was performed using silicone discs. The biofilm eradication performance of PRMSE in combination with ciprofloxacin is presented in FIG. 4; viable cell recoveries from the silicone discs after exposure to different combinations of PRMSE and ciprofloxacin were evaluated. PRMSE alone did not show significant eradication of monoculture biofilm on silicone discs for any of the tested strains, while PRMSE in combination with sub-lethal concentration of ciprofloxacin had significant biofilm eradication effect with synergistic interaction at higher concentration of ciprofloxacin (p<0.05). These results are correlated with the above-mentioned anti-biofilm activity of PRMSE.

In an effort to elucidate the mechanism(s) for the observed synergistic interactions, the change in bacterial outer membrane permeability was quantified using 1-N-phenylnapthylamine (NPN) as an indicator. The results show that both PRMSE and catechol, at sub-lethal concentrations, increased membrane permeability in all tested strains (Table 5, FIG. 5).

TABLE 5

Biological effects of PRMSE and catechol

| Bacterial strains | Effects based on bioassays | Untreated cells | Phenolic extract PRMSE | Pure compound catechol | Positive controls[e] | | |
|---|---|---|---|---|---|---|---|
| | | | | | gentamicin (µg mL$^{-1}$) | CCCP | CTAB |
| E. coli CFT073 | Minimum permeabilization concentration [mg mL$^{-1}$] (NPN assay) [a] | — | 1.6 | 0.06 | 0.006 | NA[f] | NA |
| | % Reduction in efflux pump activity [b] | 36.9 | 22.7 | 34.3 | NA | 15.8 | NA |
| | % cells with uncompromised membrane (BacLight assay)[c] | 100 | 88.7 | 68 | NA | NA | 0 |
| | Bacterial colony forming ability (Δ log CFU mL$^{-1}$)[d] | 0 | 0.8 | 2.3 | NA | NA | 5.7 |

TABLE 5-continued

Biological effects of PRMSE and catechol

| Bacterial strains | Effects based on bioassays | Untreated cells | Phenolic extract PRMSE | Pure compound catechol | Positive controls[e] gentamicin ($\mu g\ mL^{-1}$) | CCCP | CTAB |
|---|---|---|---|---|---|---|---|
| P. mirabilis HI4320 | Minimum permeabilization concentration [$mg\ mL^{-1}$] | — | 1.6 | 1 | 0.013 | NA | NA |
| | % Reduction in efflux pump activity | 35.9 | 23.4 | 33.9 | NA | 14.5 | NA |
| | % cells with uncompromised membrane | 100 | 72.6 | 50.3 | NA | NA | 0 |
| | Bacterial colony forming ability (Δ log CFU $mL^{-1}$) | 0 | 1.2 | 3.2 | NA | NA | 4.5 |
| P. aeruginosa PAO1 | Minimum permeabilization concentration [$mg\ mL^{-1}$] | — | 0.8 | 0.5 | 1 | NA | NA |
| | % Reduction in efflux pump activity | 37.6 | 22.3 | 35.8 | NA | 19.3 | NA |
| | % cells with uncompromised membrane | 100 | 87.9 | 80.4 | NA | NA | 0 |
| | Bacterial colony forming ability (Δ log CFU $mL^{-1}$) | 0 | 0.9 | 1.5 | NA | NA | 5.1 |
| P. aeruginosa PA14 | Minimum permeabilization concentration [$mg\ mL^{-1}$] | — | 0.8 | 0.5 | 1 | NA | NA |
| | % Reduction in efflux pump activity | 30.9 | 19 | 29.9 | NA | 17 | NA |
| | % cells with uncompromised membrane | 100 | 89.1 | 78.6 | NA | NA | 0 |
| | Bacterial colony forming ability (Δ log CFU $mL^{-1}$) | 0 | 0.9 | 1.9 | NA | NA | 4.9 |

[a] Assay was performed at sub-MIC of extract and pure compound compared to reference antibiotic (gentamicin at above and below MICs), these concentrations led to maximal increase in NPN (1-N-phenylnapthylamine) uptake based on fluorescence intensity recorded.
[b] The ratio of green to red fluorescence was normalized to the untreated control and expressed as a percentage of the control. Cells were treated at 4 × MIC of pure compound and extract for 10 min.
[c] Reduction in fluorescence intensity as a percentage of that at the first time point of recording. Cells were treated overnight at 0.25 times the MIC of pure compound and extract.
[d] Bacterial colonies were counted from LB agar plate, and the log decrease in CFU/mL compared to the untreated control was calculated.
[e] CCCP: carbonyl cyanide m-chlorophenylhydrazone (100 μM), CTAB: cetyltrimethyl-ammonium bromide (10 μM).
[f] NA, not applicable.

Figure 5:
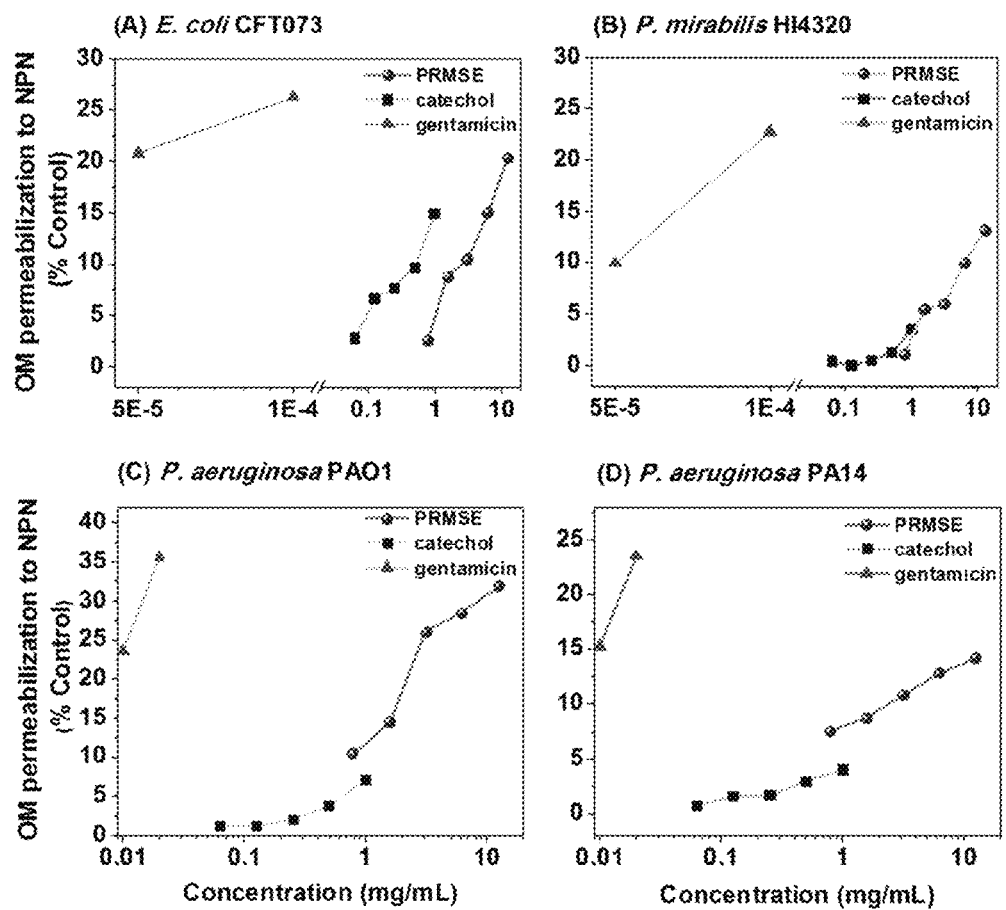
FIG. 5 illustrates PRMSE, catechol, and gentamicin-mediated NPN uptake in (FIG. 5A) *E. coli* CFT073, (FIG. 5B) *P. mirabilis* HI4320, (FIG. 5C) *P. aeruginosa* PAO1 and (FIG. 5D) *P. aeruginosa* PA14. Bacterial cells were pre-treated with 1 mM N-ethylmaleimide (NEM) in 5 mM HEPES buffer (pH 7.2) and incubated at room temperature in the presence or absence (control) of various sub-MICs of PRMSE, catechol, and gentamicin. Enhanced uptake of NPN was determined by an increase in fluorescence (ex/em: 350 nm/420 nm) caused by partitioning of NPN into the hydrophobic interior of the outer membrane.

These effects were similar to the known outer membrane permeabilizing effect of gentamicin (FIG. 5).

Bacterial cell membrane damage was further examined using the BacLight assay. As shown in Table 5, catechol and PRMSE exhibited moderate membrane disruptive effects. The cells exposed to PRMSE or catechol were also tested for their ability to form colonies on solid agar medium. Catechol reduced the number of CFUs compared to the negative control (≥1.5 log reduction in CFU mL-1 for E. coli CFT073, P. mirabilis HI4320 and P. aeruginosa PA14) during the 10 min exposure period, whereas PRMSE had a weak effect on the colony forming ability of chosen strains. The CFU measurement correlates well with the BacLight results; however, because bacterial membrane damage is not necessarily a lethal event, the severity of the effect reflected by each assay is different.

The effect of PRMSE and catechol on inhibition of bacterial drug resistance efflux pump was investigated using the ethidium bromide (EtBr) efflux pump assay. PRMSE exhibited significant inhibitory effect on efflux pump for all bacterial strains with values comparable to the positive control CCCP, which is an established proton motive force modulator (Table 5). There was weak reduction in fluorescence intensity for cells treated with PRMSE indicating accumulation of EtBr in the cell as a result of efflux pump inhibition. Cells treated with catechol also exhibited reduction in EtBr efflux, but to a lesser extent than cells treated with PRMSE (Table 5).

To explore the genetic basis for the synergy in antimicrobial activity observed between PRMSE and antibiotics, as well as the effect of PRMSE on bacterial biofilms, transcriptional analysis was performed using qRT-PCR to observe the differential expression of genes associated with bacterial motility, virulence, drug resistance, adhesion and biofilm formation for each of the four bacterial strains. The results in FIG. 6 indicate that PRMSE, at sub-lethal concentrations, repressed the expression of genes associated with multiple drug resistance (emrA, acre and marC in CFT073; acrA and marC in HI4320; oprM, mexA and mexX in PAO1 and PA14), motility (fliC, flhD, motB, fimH, fimA, papA2 in CFT073; flaA, flhD in HI4320; fliC, fleQ in PAO1 and PA14), virulence determinants (chuA in CFT073; cysJ in HI4320; plcH, phzS and pvdA in PAO1 and PA14), adhesion (fimH, fimA, papA2 in CFT073; atfB in HI4320; cupA1, pelA in PAO1 and PA14) and biofilm formation (uvrY in CFT073; ureD in HI4320; lasB in PAO1 and PA14). Transcriptional analysis confirms the trends observed with the biofilm assay (i.e., biofilm inhibition in the presence of PRMSE correlates with down-regulation of biofilm associated genes) and antibiotic synergy tests (i.e., down-regulation of multiple drug resistance genes correlates with increased antibiotic susceptibility in the presence of PRMSE).

Figure 7:
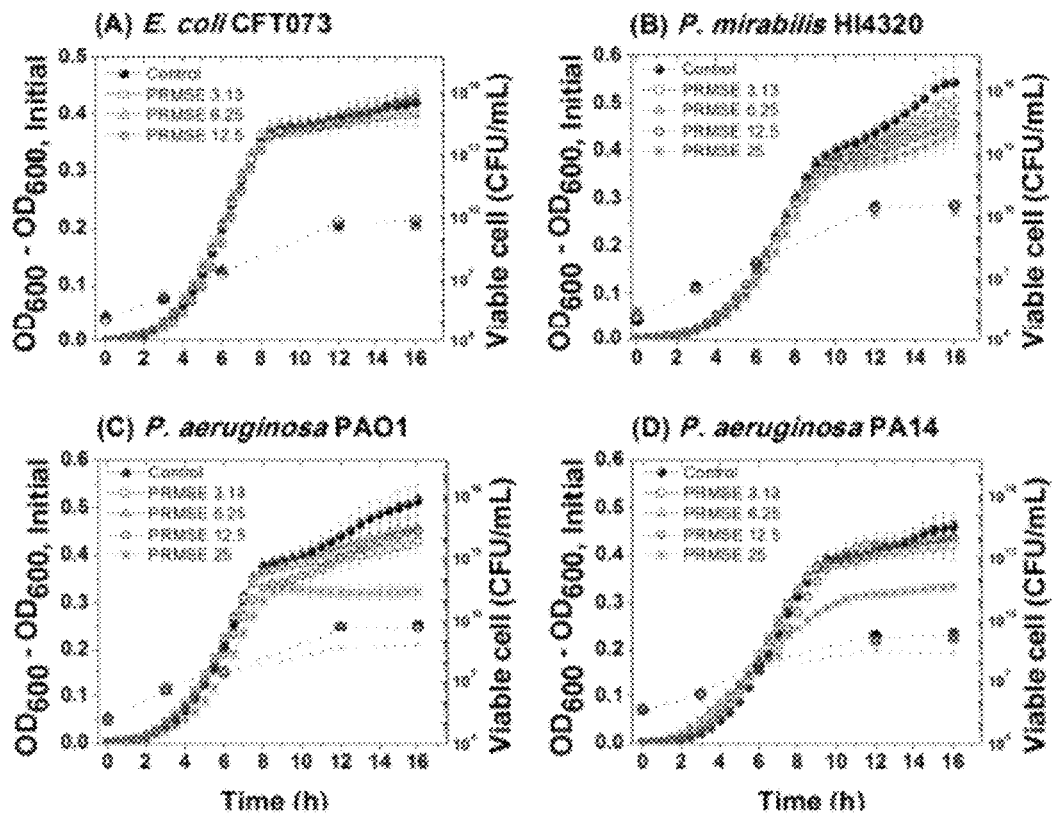
FIG. 7 illustrates growth curves in M9 minimal medium for (FIG. 7A) *E. coli* CFT073, (FIG. 7B) *P. mirabilis* HI4320, (FIG. 7C) *P. aeruginosa* PAO1 and (FIG. 7D) *P. aeruginosa* PA14, in the presence of PRMSE. Bacterial growth ($OD_{600}$) was monitored at 37° C. for 16 h in M9 minimal medium. Error bars represent the standard deviation of values obtained from four replicates of two independent experiments performed on different days. Viable cell population was monitored at the same culture conditions and determined by serial dilution in PBS and plating on LB agar plates. Abbreviations: PRMSE.x, MS polyphenolic extract at x mg $mL^{-1}$ (e.g., PRMSE 25 indicates polyphenolic-rich MS extract at 25 mg $mL^{-1}$).

PRMSE was used at sub-lethal concentrations for this experiment and does not affect bacterial growth of all four strains (FIG. 7). This is important because conditions that affect growth can inhibit gene expression. Based on these results, it can be concluded that the observed differences in gene expression were due to the presence of PRMSE and not due to growth inhibition by this extract.

Figure 8:
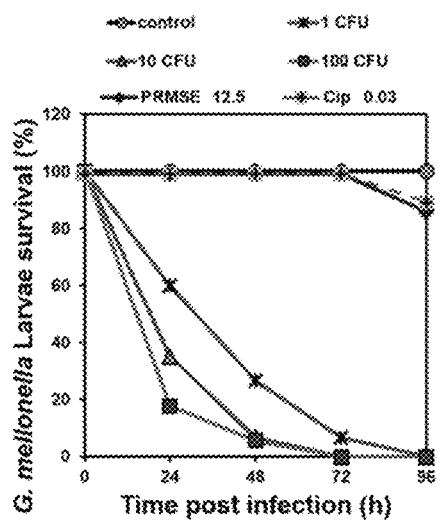
FIG. 8 illustrates *G. mellonella* larvae survival over time when injected with *P. aeruginosa* PA14, PRMSE or ciprofloxacin (Cip). The larvae were injected separately with bacteria (1-100 CFU per larva), PRMSE (12.5 mg/mL) or ciprofloxacin (0.03 µg/mL) and monitored for their survival at 28° C. Each data set is representative of experiments with five larvae per condition in triplicate.

*Galleria mellonella* larvae have emerged as an ideal host model due to a number of characteristics, such as a high degree of functional and structural homology to the innate immune systems of mammals, and possess characteristics to understand virulence mechanisms of human pathogens in vivo (Cook and McArthur, 2013, Virulence, 4:350-353). *P. aeruginosa* is an opportunistic human pathogen that displays an extraordinarily broad host range to infect vertebrates, non-vertebrate insects, and plants (Apidianakis and Rahme, 2009 Nature Protocol, 4:1285-1284). To determine the effective larvae killing dose of *P. aeruginosa* PA14, the survival of *G. mellonella* larvae injected into the hemolymph (blood-like fluid) with different cell densities of *P. aeruginosa* PA14 was observed. As shown in FIG. 8, a single PA14 bacterium decreased *G. mellonella* larvae survival within 96 h post-infection period. Optimal killing of *G. mellonella* larvae for use in the anti-infection assay was observed with a dose of 10 CFU/larva, as this led to effective larvae killing of >60% at 24 h post-infection (FIG. 8). This condition was used for further studies with PRMSE.

The individual effects of PRMSE and ciprofloxacin on the survival of *G. mellonella* larvae after injection was analyzed. PRMSE and ciprofloxacin, at sub-MICs of 12.5 mg/mL and 0.03 µg/mL, respectively, had no killing effect on *G. mellonella* larvae within 72 h post-infection period (FIG. 8). These observations show that PRMSE and ciprofloxacin at sub-MICs are safe for *G. mellonella* larvae.

Figure 9:
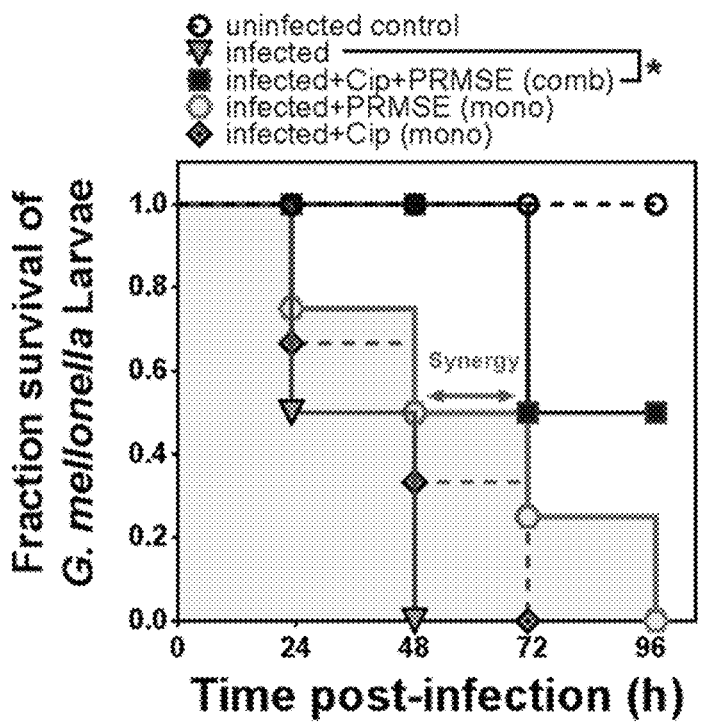
FIG. 9 illustrates the in vivo efficacy of PRMSE or ciprofloxacin (Cip) mono- and combination (comb) therapies analyzed for the protection of *G. mellonella* larvae from PA14 infection. Larvae were infected with bacteria (10±3 CFU per larva) and after 2 h injected with PRMSE (12.5 mg/mL) or ciprofloxacin (0.03 µg/mL), alone and in combination, and monitored for their survival at 28° C. Synergy between PRMSE and ciprofloxacin to protect *G. mellonella* larvae against PA14 infection is shown with arrows. Each data set represents one experiment with five larvae per condition in triplicate, the experiment repeated twice (*P<0.05, Mantel-cox test, n=6).

To explore the efficacy of PRMSE and ciprofloxacin to limit *P. aeruginosa* infection in vivo, PRMSE and ciprofloxacin were injected in *G. mellonella* larvae as mono- and combination therapies at sub-MICs. *G. mellonella* larvae were infected by injection with a lethal dose of PA14 strain (10±3 cells from exponential cultures) and incubated at 28° C. for 2 h. These infected *G. mellonella* larvae were injected a second time with or without PRMSE (12.5 mg/mL), with or without the antibiotic ciprofloxacin (0.03 µg/mL) at 2 h post-infection period. As shown in FIG. 9, the median survival of *G. mellonella* larvae infected with only *P. aeruginosa* PA14 was 36 h (without PRMSE or ciprofloxacin), which is significantly lower ($X^2=4.9$, df=1, p<0.05) than that measured for the combination therapy of PRMSE and ciprofloxacin (84 h), based on the comparison of survival curves. Monotherapy of ciprofloxacin at sub-MIC fails to protect *G. mellonella* larvae against *P. aeruginosa* PA14 infection, but monotherapy of PRMSE shows moderate protection to *G. mellonella* larvae against PA14 infection with median survival of 60 h. Overall, these results show that PRMSE protects *G. mellonella* larvae from *P. aeruginosa* infection. They also clearly demonstrate that PRMSE acts in synergy with ciprofloxacin to protect *G. mellonella* larvae from *P. aeruginosa* infection.

Figure 10:
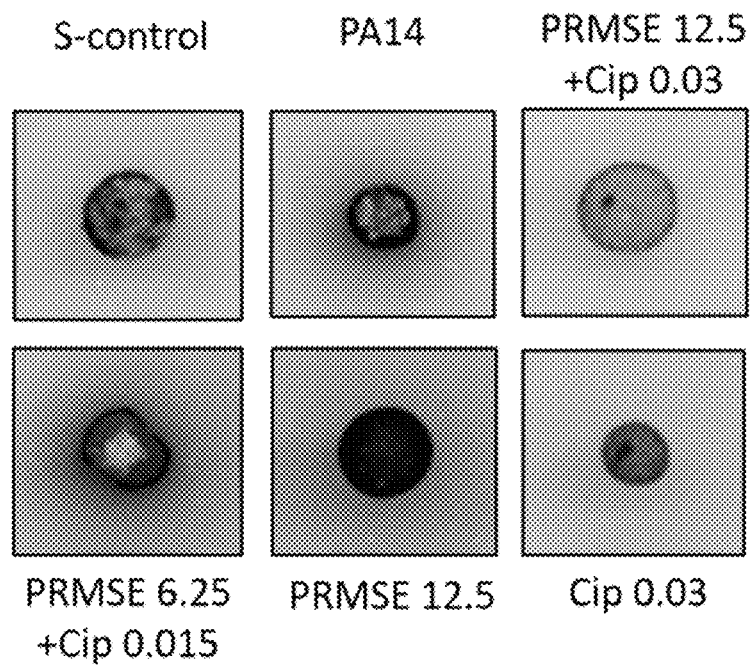
FIG. 10 illustrates the in vitro analysis of hemolymph recovered from *G. mellonella* larvae treated with PRMSE or ciprofloxacin (Cip), alone and in combination. Larvae were injected with PRMSE (mg/mL) or Cip (µg/mL) alone and in combination, and hemolymph recovered 3 h after treatment were spotted on *Pseudomonas* isolation agar plates previously inoculated with PA14 cells to produce a lawn of confluent growth. The plate was observed after 24 h of incubation at 37° C. The experiment was performed with three larvae per each condition in triplicate. S-control: saline control.

The difference in the treated or untreated *P. aeruginosa* PA14 cells present in the hemolymph (blood-like fluid) of *G. mellonella* larvae after the injection may be due to modified survival of the bacteria in the hemolymph during incubation. Another possibility is that PRMSE induces the immune response or transformations of antimicrobial compounds into toxic materials in the larval hemolymph during incubation. To address these possibilities, an additional set of larvae were injected with 5 µL saline solution with or without PRMSE, with or without ciprofloxacin (at selected concentrations in ng per larva). The larval hemolymph was recovered at 3 h post-injection and spotted on the freshly inoculated cells of PA14 to analyze growth inhibition by recovered hemolymph. As shown in FIG. 10, at the end of incubation period, recovered larval hemolymph turned to brown colored spots on agar plate, possibly due to coagulation or clotting of hemolymph proteins, but no inhibition zone in the lawn of PA14 colonies was observed. Thus, larval hemolymph recovered from larvae treated with or without PRMSE, with or without ciprofloxacin, had no effect on *P. aeruginosa* PA14 growth in vitro, further confirming that the observed effect of PRMSE on pathogenicity of PA14 strain is due to inhibition of virulence rather than a growth-inhibitory effect.

Figure 11:
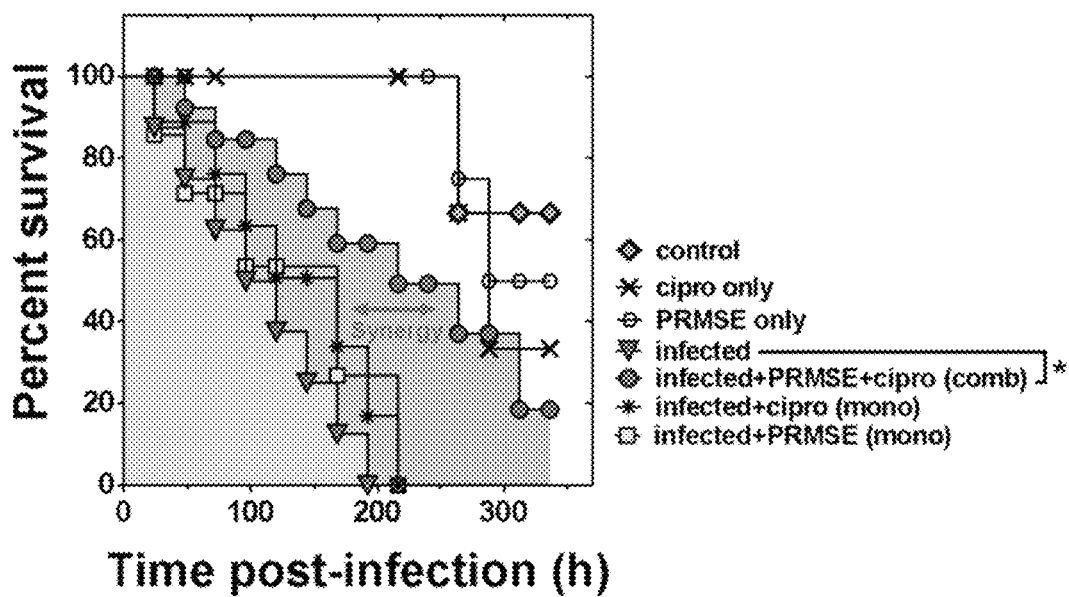
FIG. 11 illustrates the in vivo anti-virulence synergy of PRMSE (6.25 mg $mL^{-1}$) with ciprofloxacin (0.015 µg $mL^{-1}$) for the protection of *D. melanogaster* against *P. aeruginosa* PA14 infection. Mortality was scored daily for 14 days. Synergy between PRMSE and ciprofloxacin to protect *D. melanogaster* flies against PA14 infection is shown with arrows. Results represent measurements from experiments performed with duplicates, twice (*p<0.01, Log-rank Mantel-cox test).

The *Drosophila melanogaster* fly has emerged as an another ideal host model for an understanding of *P. aeruginosa* virulence mechanisms and immune response in vivo because of the high degree of homology between vertebrates and fly innate immune systems (Apidianakis and Rahme, 2009 Nature Protocol 4:1285-1284). Similar to the in vivo assay with *G. mellonella* larvae, the individual effects of PRMSE and ciprofloxacin on the survival of *D. melanogaster* flies infected with *P. aeruginosa* PA14 after feeding them with extract or antibiotic were analyzed. PRMSE and ciprofloxacin, at sub-MICs of 6.25 mg/mL and 0.015 µg/mL, respectively, had no killing effect on *D. melanogaster* flies within 264 h post-infection period (FIG. 11). These observations show that PRMSE and ciprofloxacin individually at sub-MICs are safe for *D. melanogaster* flies.

To explore the synergistic efficacy of PRMSE and ciprofloxacin to limit *P. aeruginosa* infection in vivo, *D. melanogaster* flies were fed with PRMSE and ciprofloxacin as mono- and combination therapies at sub-MICs in the presence of *P. aeruginosa* PA14. *D. melanogaster* male flies were starved of food and water for 5-6 h before the infection with PA14, without and with mono- and combination therapies. As shown in FIG. 11, the median survival of *D. melanogaster* male flies infected with only *P. aeruginosa* PA14 was 108 h (without PRMSE or ciprofloxacin), but 216 h with the combination therapy of PRMSE and ciprofloxacin, which is significantly ($X^2=7.9$, df=1, p<0.01) higher based on the comparison of survival curves. Monotherapy of PRMSE or ciprofloxacin at sub-MIC fails to protect *D. melanogaster* against *P. aeruginosa* PA14 infection. This result indicates that synergy between PRMSE and ciprofloxacin protects *D. melanogaster* against *P. aeruginosa* PA14 infection.

Figure 12:
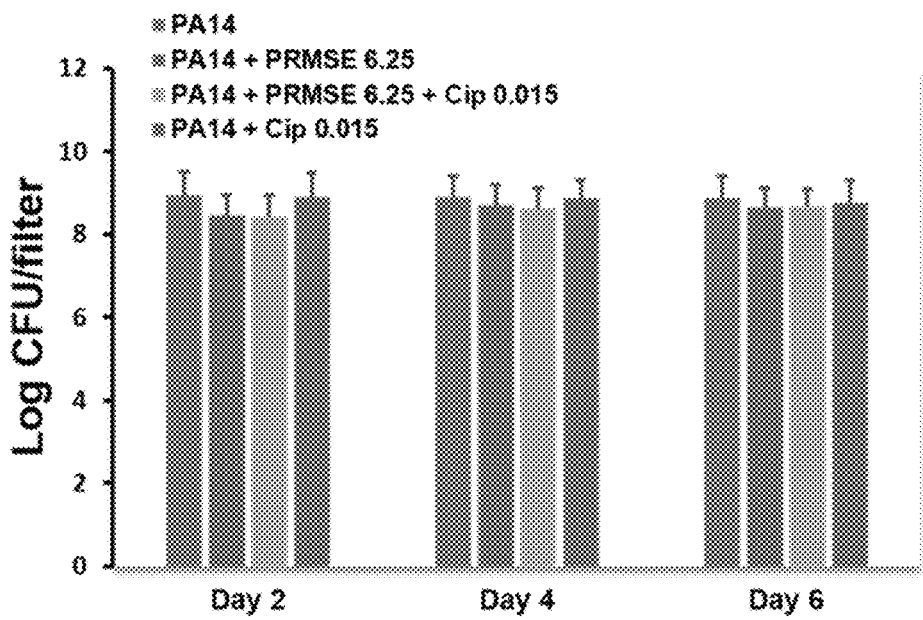
FIG. 12 illustrates the survival of *P. aeruginosa* PA14 on sucrose filters during fly feeding assays. Total viable bacterial counts per filter were determined every second day for filters containing bacterial cells on sucrose agar. PA14 cells on filter were untreated or treated with PRMSE (6.25 mg mL-1) or ciprofloxacin (0.015 µg mL-1) alone and in combination. Average data represent data from experiment performed in triplicate and error bars represent S.D.

The difference in the treated or untreated PA14 strain's ability to kill *D. melanogaster* in this feeding assay may have been due to modified survival of the bacteria on the filter papers used for exposure during incubation. To address this possibility, the survival of PA14 on the paper discs without and with PRMSE and ciprofloxacin as mono- and combination therapies under the same conditions as the fly feeding assay was analyzed. There was no significant difference in culturability of the PA14 cells on the filter paper discs in the absence and presence of mono- and combination therapies during incubation of six days (FIG. 12), indicating that an alteration in survival ability of bacteria could not account for the observed differences in fly killing.

Figure 13:
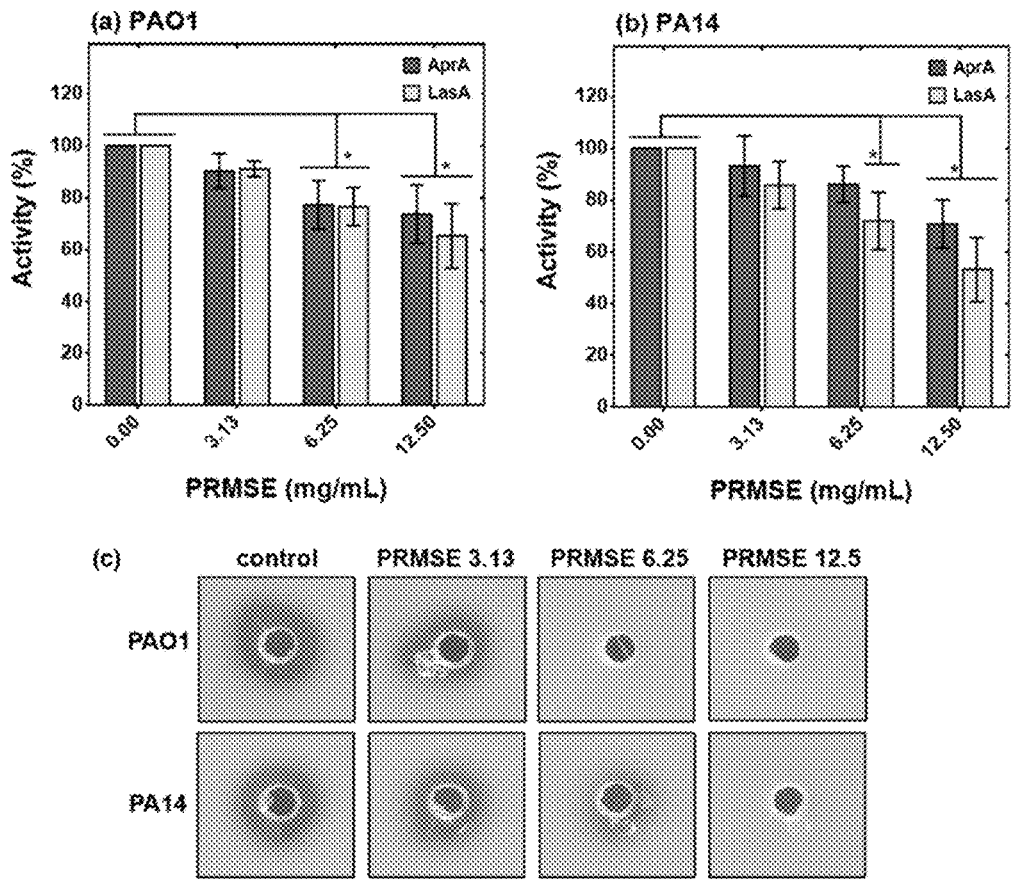
FIG. 13 illustrates the inhibition of virulence determinants of *P. aeruginosa* PAO1 and PA14 strains in the absence or presence of different PRMSE concentrations (mg/mL).

The effect of PRMSE on virulence determinant enzymes of PAO1 and PA14 was investigated at different concentrations. At the selected concentrations, bacterial growth was not inhibited. As shown in FIGS. 13A and 13B, treatment with PRMSE significantly (P<0.05) inhibited the staphylolytic (LasA) and alkaline proteolytic (AprA) activities of *P. aeruginosa* PAO1 and PA14. Total proteolytic activities of *P. aeruginosa* PAO1 and PA14 treated without and with PRMSE were analyzed on skim milk agar plate. There was no halo formation around the wells loaded with supernatant of sample with 12.5 mg/mL PRMSE compared to the untreated control sample, indicating inhibition of total proteolytic activity. Treatment with PRMSE inhibited total proteolytic activity of PAO1 and PA14 strains (FIG. 13C). This result indicates that PRMSE inhibits activities of virulence determinant enzymes of *P. aeruginosa*.

Figure 14:
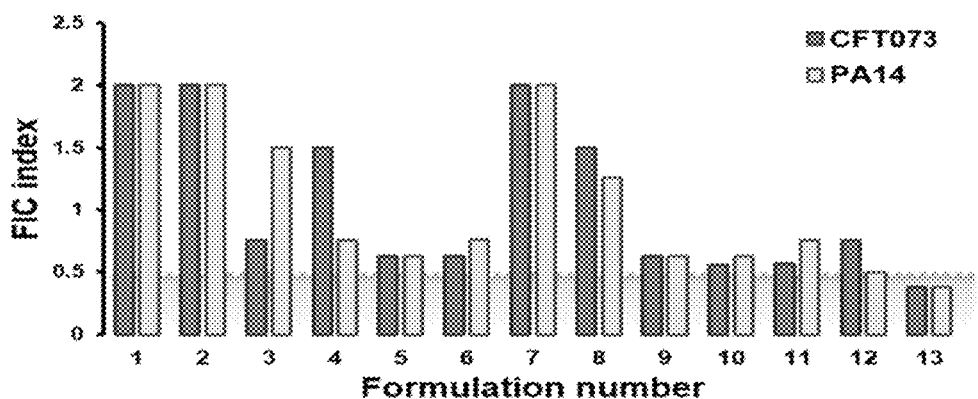
FIG. 14 illustrates the interactions of ciprofloxacin and different phenolic formulations for the growth inhibition of *E. coli* CFT073 and *P. aeruginosa* PA14. FIC index ≤0.5 indicates synergistic interaction.

A checkerboard assay was performed using different combinations of the pure phenolic compounds identified in PRMSE, i.e., gallic acid, catechol, catechaldehyde, 3-hydroxybenzoic acid, vanillin and syringaldehyde. Interaction was analyzed with ciprofloxacin against *E. coli* CFT073 and *P. aeruginosa* PA14. Formulation-1 represents relative concentrations of phenolics as determined in PRMSE by HPLC (Table 6). Additional different formulations were prepared as variations of Formulation-1 and assessed for synergistic interaction. As shown in FIG. 14, the corresponding FICI values of Formulation-13 were <0.5, indicating synergistic interaction with ciprofloxacin against both CFT073 and PA14. The FICI values for Formulations 1-11 were between >0.5 and ≤4 indicating no interaction or indifference. Formulation-12 shows synergy with ciprofloxacin against PA14 (0.5 FIC index), but not against CFT073 (>0.5 FIC index).

matrix, nevertheless, resistance has been reported in *P. aeruginosa* and *E. coli* biofilms. This suggests that the mechanism of resistance of these biofilms to ciprofloxacin goes beyond poor drug penetration and may be due to the presence of persister or resistant cells. Moreover, PRMSE exhibits synergy with ciprofloxacin for eradication of monoculture biofilm from silicone substrates, showing the applicability of PRMSE as a biofilm eradication strategy along with antibiotics.

Further, PRMSE, at sub-lethal concentrations, can increase the uptake of NPN into the cell outer membrane, indicating its ability to permeabilize the membrane (Table 5). Results provided herein indicate that outer membrane permeabilization by PRMSE is achieved without altering the cell membrane integrity.

TABLE 6

Concentrations (mg/mL) of phenolic compounds in different formulations for checkerboard assay

| Phenolic compounds | Formulation # | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| gallic acid | 8.52 | 4.26 | 4.26 | 4.26 | 0.65 | 0.65 | 0.30 | 4.26 | 2.13 | 0.65 | 0.65 | 1.3 | 0.65 |
| catechol | 0.30 | 0.30 | 0.65 | 0.30 | 0.65 | 0.65 | 0.30 | 0.30 | 0.65 | 0.65 | 0.65 | 0.65 | 0.65 |
| catechaldehyde | 0.02 | 0.02 | 0.02 | 0.04 | 0.04 | 0.30 | 0.65 | 0.02 | 0.04 | 0.04 | 0.12 | 0.65 | 0.65 |
| 3-hydroxybenzoic acid | 0.06 | 0.06 | 0.06 | 0.06 | 0.06 | 0.06 | 0.06 | 0.06 | 0.12 | 0.12 | 0.12 | 0.12 | 0.12 |
| vanillin | 0.002 | 0.002 | 0.002 | 0.002 | 0.002 | 0.002 | 0.002 | 0.020 | 0.04 | 0.04 | 0.04 | 0.04 | 0.04 |
| syringaldehyde | 0.001 | 0.001 | 0.001 | 0.001 | 0.30 | 0.002 | 0.002 | 0.010 | 0.02 | 0.02 | 0.02 | 0.02 | 0.02 |

In summary, the antimicrobial, anti-biofilm, and anti-virulence effects of a cocktail of phenolic compounds extracted from maple syrup (PRMSE) against a range of pathogenic bacteria is disclosed. PRMSE potentiate antibiotic susceptibility in both planktonic and biofilm modes of growth, which could be partially due to its ability to permeabilize the bacterial membrane, inhibit multidrug resistance efflux pumps, and downregulate genes associated with multidrug resistance. Amongst the four tested phenolic constituents of PRMSE, results indicate that catechol plays a key role in the synergistic activity of PRMSE with ciprofloxacin.

Phenolic extracts of maple syrup have been reported to exhibit antioxidant and anticancer activity linked with the presence of diverse phytochemical constituents, including phenylpropanoid. Of the 51 known metabolites in maple syrup (from *A. saccharum*), four compounds were investigated in more detail. Combination of catechol with ciprofloxacin, gallic acid, catechaldehyde or syringaldehyde, and the combination of gallic acid with catechaldehyde, exhibited a synergistic antimicrobial effect against all chosen strains in vitro (Tables 3 and 4). Catechol has been previously reported to interact synergistically with other phenolic compounds in terms of antioxidant capacity. Moreover, catechol is made synthetically and can be readily available for potential use as a disinfectant.

Figure 2:
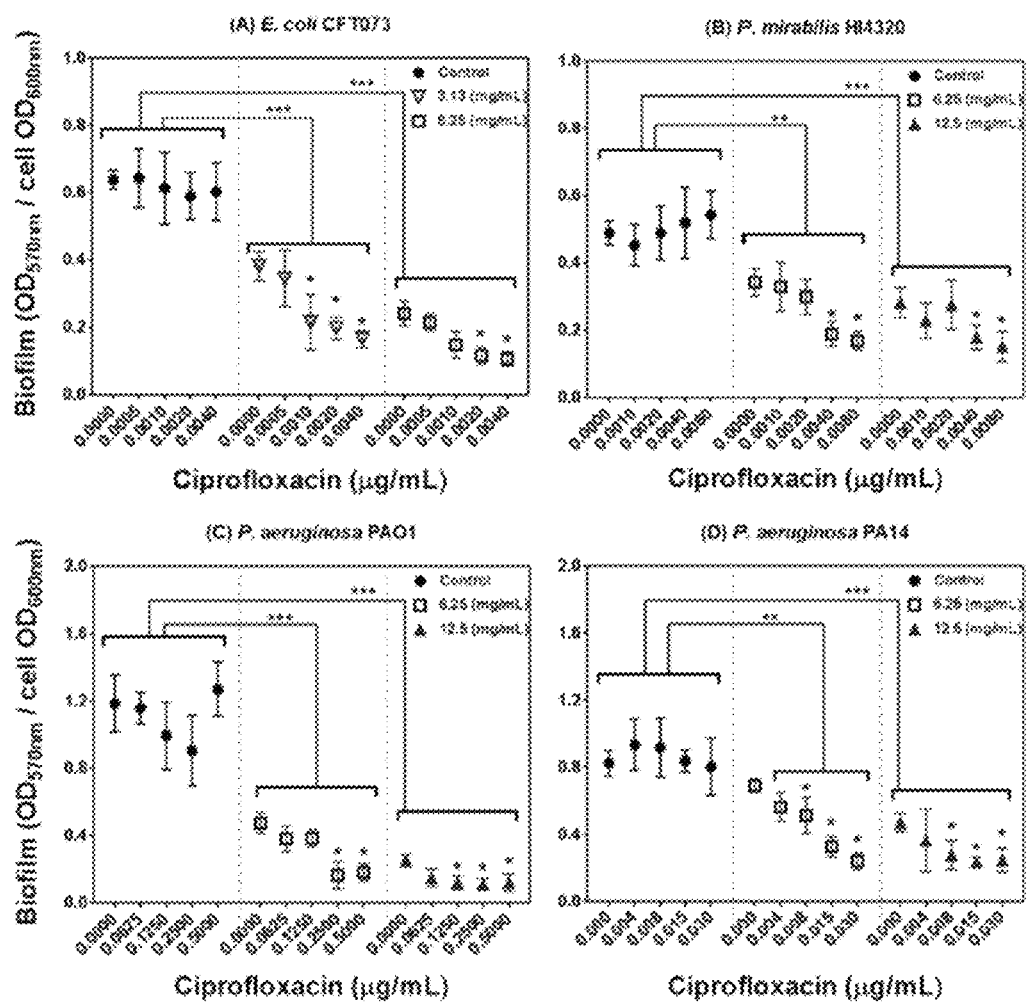
FIG. 2 illustrates the effect of PRMSE, with and without ciprofloxacin, on biofilm formation of (FIG. 2A) *E. coli* CFT073, (FIG. 2B) *P. mirabilis* HI4320, (FIG. 2C) *P. aeruginosa* PAO1 and (FIG. 2D) *P. aeruginosa* PA14. The graph presents normalized biofilm levels ($OD_{570}/OD_{600}$) versus different sub-inhibitory concentrations of ciprofloxacin for each strain grown in LB medium (Control) or in LB medium amended with sub-inhibitory concentrations of PRMSE (3.13, 6.25 and 12.5 mg $mL^{-1}$).
Figure 6:
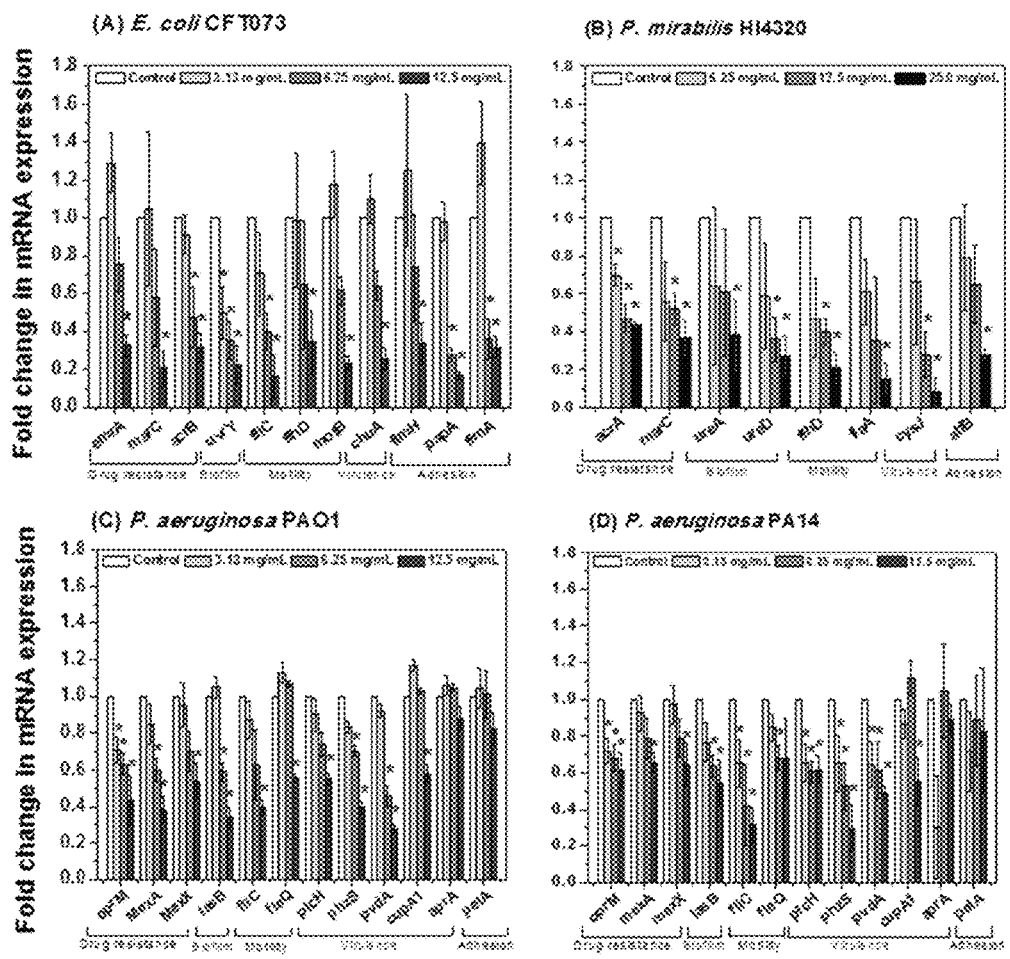
FIG. 6 illustrates the effect of PRMSE on expression of virulence genes for (FIG. 6A) *E. coli* CFT073, (FIG. 6B) *P. mirabilis* HI4320, (FIG. 6C) *P. aeruginosa* PAO1, and (FIG. 6D) *P. aeruginosa* PA14. Error bars are the standard deviation of values obtained from three replicates. All gene expressions were normalized to the corresponding house-keeping gene (gapA of *E. coli* CFT073, rpoA of *P. mirabilis* HI4320, rpoD of *P. aeruginosa* PAO1 and PA14) and then related to the normalized expression level of the same gene in the control.

PRMSE and catechol exhibit anti-biofilm activity against the four pathogenic strains examined. Genes associated with biofilm formation (uvrY, fimH, fimA and papA2 of *E. coli*, ureD, ureA and atfB of *P. mirabilis*, and lasB and cupA1 of *P. aeruginosa*) were downregulated upon supplementation with PRMSE. In addition, PRMSE and catechol synergized with ciprofloxacin at sub-lethal concentrations to further inhibit the formation of biofilms (FIGS. 2 and 3). Ciprofloxacin has good penetration properties in the biofilm Multidrug efflux pumps of Gram-negative bacteria that traverse both the outer and inner membranes make a key contribution to intrinsic antimicrobial resistance. PRMSE showed significant inhibition of the EtBr transport across the cell envelope, which indicates a decreased activity of bacterial multidrug resistance efflux pumps (Table 5) and reduction in expression of genes associated with multi-drug resistance (FIG. 6). Active efflux involves multi-drug resistance efflux pump assemblies in the bacterial cell membranes that transport structurally unrelated compounds, including different classes of antibiotics, antiseptics, and cationic dyes, such as ethidium bromide (EtBr) and acriflavin. Thus, the observed inhibition of efflux pumps is of interest, as it results in (i) increased intracellular drug concentration, (ii) restoration of drug activity against resistant strains, (iii) minimization of further development of resistance, and (iv) reduced biofilm formation.

Accordingly, PRMSE increases the potency of conventional antibiotics against planktonic and biofilm cells of four pathogenic bacterial strains through a strong synergistic effect. Membrane permeabilization and efflux pump inactivation contribute to this antibacterial and anti-biofilm synergy. In addition, catechol is the major contributor to the anti-biofilm and antibacterial synergy effects. It is thus provided the combined use of PRMSE (or its active component catechol) with antibiotics to target bacterial biofilms. By combining antibiotics with PRMSE that exhibit synergistic interaction, it is possible to decrease the dosage of antibiotics used to eradicate bacterial biofilms.

A synergistic combination of antibiotic with catechol inhibited the growth of tested clinical strains in vitro. Furthermore, combinations of catechol with selected phenolic components of maple syrup were highly synergistic against the growth of clinical strains. Accordingly, the combination of phenolics from PRMSE and an antibiotic is an effective anti-bacterial therapy, and imparts prospective biological property to maple syrup.

It is further provided that PRMSE alone or ciprofloxacin alone at sub-MICs are safe for *Galleria mellonella* larvae and *Drosophila melanogaster* flies. Combination therapy of PRMSE combined with ciprofloxacin shows synergy to protect *G. mellonella* larvae and *D. melanogaster* flies from *P. aeruginosa* PA14 infection.

Monotherapy of ciprofloxacin at sub-MIC fails to protect *G. mellonella* larvae and *D. melanogaster* flies against *P. aeruginosa* PA14 infection, but monotherapy of PRMSE at sub-MIC shows moderate protection to *G. mellonella* larvae against *P. aeruginosa* PA14 infection.

The effect of PRMSE on pathogenicity of *P. aeruginosa* PA14 strain during in vivo infection is due to inhibition of virulence rather than a growth-inhibitory effect.

The mechanisms of action protecting in vivo models against *P. aeruginosa* infection are that PRMSE (i) inhibits activities of virulence determinant enzymes of *P. aeruginosa*, (ii) inhibits multidrug efflux pump activity, (iii) increases cell membrane permeability to antibiotics, (iv) downregulates genes associated with virulence, drug resistance, biofilm formation, motility and adhesion. Accordingly, different combinations of the pure phenolic compounds previously identified in PRMSE do not show synergy with ciprofloxacin against *E. coli* CFT073 and *P. aeruginosa* PA14. Only very specific combinations of the pure compounds act similarly to the PRMSE.

Accordingly, it is provided a method of treating a bacterial infection comprising administering to a subject in need thereof a phenolic-rich extract as disclosed herein and at least one antibiotic. The subject can be for example, a human, an animal, a *Galleria mellonella* or a *Drosophila melanogaster*.

It is thus encompassed that by treating bacterial infections, the composition described herein can treat an urinary tract infection, lung infection, kidney infection, gastrointestinal infection, wound infection, acute sinusitis, skin and skin structure infections, bone and joint infections, lyme disease, typhus fever, rocky mountain spotted fever, rickettsialpox, or tuberculosis.

The present disclosure will be more readily understood by referring to the following examples which are given to illustrate the invention rather than to limit its scope.

Example I

Bacterial Strains and Preparation of PRMSE

The following organisms were used: *E. coli* strain CFT073 (ATCC 700928), *P. mirabilis* HI4320, *P. aeruginosa* PAO1 (ATCC 15692) and *P. aeruginosa* PA14 (UCBPP-PA14). Pure stock cultures are maintained at −80° C. in 30% (v/v) frozen glycerol solution. Starter cultures are prepared by streaking frozen cultures onto LB agar [LB broth: tryptone 10 g $L^{-1}$, yeast extract 5 g $L^{-1}$ and NaCl 5 g $L^{-1}$, supplemented with 1.5 w/v % agar (Fisher Scientific, ON, Canada)]. After overnight incubation at 37° C., a single colony was inoculated into 10 mL of LB broth and the culture was incubated at 37° C. on an orbital shaker at 200 rpm for time lengths specific to each experiment. LB broth was used for bacterial culture in all experiments unless otherwise specified.

All maple syrup samples (grade D, amber, production year 2013; 66° Brix syrup) were stored at −20° C. until extraction, according to a protocol described by Gonzales et al. (2012, J. Funct. Foods, 4: 185-196). Briefly, maple syrup is enriched for phenolic content by using Amberlite XAD-16 (Sigma-Aldrich Canada) resin column chromatography (C4919, bed volume of 245 mL, Sigma-Aldrich Canada). The column is subsequently extracted with methanol (Sigma-Aldrich Canada). This extract is first subjected to solvent removal under vacuum and then solubilized in 0.3% v/v DMSO to yield PRMSE. Extracts are stored at −20° C., thawed at room temperature before each experiment, and filter-sterilized using 0.22 μm PVDF membrane filters (EMD Millipore Millex™, Fisher Scientific, ON, Canada) before use. PRMSE prepared in this manner is reported to not contain any natural sugar (sucrose, glucose or fructose).

The relative level of phenolic compounds in PRMSE is estimated using HPLC, as reported in the literature (Sadiki an Martin, 2013, Food Anal. Methods, 6: 737-744). Samples are analyzed using Agilent Technologies 1200 Series analytical liquid chromatographic system, consisting of binary pumps LC-20AB, degasser DGU-20A5, column oven CTO-20 AC, auto sampler SIL-20 AC and UV SPD-M20A detector. Phenolic compounds are separated on a Zorbax SB-C18 column (4.6×150 mm, 5 μm; Agilent) at 30° C. Trifluoroacetic acid at 0.2% (phase A) and methanol (phase B) are used as eluents. The elution gradient starts with 2% phase B, increased to 50% phase B at 35 min, 80% phase B at 43 min, and held at 80% for 2 min. The injection volume is 10 μL and the flow rate is 0.5 mL $min^{-1}$. Data are collected and evaluated by the Analyst 1.4.2 Software. The analytes are identified by comparing retention times and UV spectra, recorded in the range of 200-400 nm, with the individual chromatogram of each phenolic standard. The following pure phenolic compounds can be used as standards: gallic acid, 1,2-dihydroxybenzene (catechol), 3,4-dihydroxybenzaldehyde (catechaldehyde), syringaldehyde, vanillin and 3-hydroxybenzoic acid.

Example II

Determination of Minimum Inhibitory Concentration (MIC)

MICs are determined by preparing two-fold serial dilutions of PRMSE, pure phenolic compounds, and antibiotics in Mueller Hinton broth adjusted with $Ca^{2+}$ and $Mg^{2+}$ (MHB-II, Oxoid™, Fisher Scientific, ON, Canada). A range of concentration of antibiotics, ciprofloxacin (0.0003-0.25 μg $mL^{-1}$) and carbenicillin (0.5-512 μg $mL^{-1}$), are chosen due to their known potency against all four bacterial strains. Dilutions are prepared in flat bottom, 96 well microtitre plates (Falcon™, Corning™, Fisher Scientific, ON, Canada). Each well of a microtitre plate is then inoculated with the desired bacterial strain (grown in MHB-II and diluted to 106 CFU $mL^{-1}$) and the plate is incubated at 37° C. for 18 h under static conditions. Bacterial growth is assessed by (i) monitoring the optical density of the cell suspension in each well at 600 nm ($OD_{600\ nm}$), and (ii) the resazurin microtitre plate assay. In the resazurin microtitre plate assay, each well of a microtitre plate is supplemented with 20 μM resazurin, incubated in the dark for 20 min at room temperature, followed by fluorescence measurements at ex/em 570/590 nm using a TECAN Infinite M200 Pro microplate reader (Tecan Group Ltd., Switzerland). The lowest concentration of a compound able to prevent increase in $OD_{600}$ nm and resazurin fluorescence intensity is recorded as the MIC for that compound.

Example III

Checkerboard Microdilution Assay

The checkerboard microdilution assay is used for evaluation of in vitro antimicrobial synergy between two compounds (i.e., antibiotic/PRMSE, antibiotic/pure phenolic compound, and pure phenolic compounds with each other). Two-fold serial dilutions are prepared in MHB-II for each of the two compounds under study. The serial dilutions are then loaded into 96 well plates to achieve combinations having different concentrations of each of the two compounds. Each well is subsequently inoculated with $10^6$ CFU mL$^{-1}$ of the desired bacterial strain and incubated at 37° C. for 18 h under static conditions. The Fractional Inhibitory Concentration Index (FICI) for each combination is calculated by using the following formula:

$$FIC_{component\ 1} = MIC_{component\ 1,\ in\ combination} / MIC_{component\ 1, alone}$$

$$FICI = FIC_{component\ 1} + FIC_{component\ 2}$$

The FICIs are interpreted as follows: FICI of ≤1.5 (synergy); 0.5<FICI ≤1 (no interaction/indifference); FICI of >4 (antagonism).

Example IV

Biofilm Assays

Biofilm formation is quantified using the standard microtitre plate model. Briefly, overnight cultures (LB broth, 37° C., 200 rpm) are diluted 1:100 (v/v) into fresh LB broth (with or without PRMSE or catechol), to 106 CFU mL$^{-1}$. Aliquots (100 µL) of these cultures are transferred into the wells of polystyrene, flat bottom, non-treated 96 well plates (Falcon™, Corning™), in triplicate. For all assays, biofilms are allowed to develop for 16 h at 37° C. under static conditions, after which $OD_{600}$ values are recorded, the spent broth is decanted from the wells, and the wells are gently rinsed three times with DI water. The washed biofilm is stained with crystal violet (CV). For CV stain assay, 100 µL of 0.1% (w/v) CV is loaded in each well and the plates are incubated for 15 min under static conditions at room temperature. The wells are subsequently rinsed with DI water to remove excess dye and the CV adsorbed to the biomass in each well is solubilized in 100 µL of absolute ethanol for 10 min. The solubilized CV is then quantified (as $OD_{570}$) using a microplate reader. Control experiments are performed with cell-free broth to adjust for the background signal.

In vitro assessment of PRMSE for eradication of pre-formed biofilm on low-surface energy silicone surfaces (a model biomaterial) is performed using the method described in Rosenblatt et al. (2013, Antimicrob. Agents Chemother., 57: 3555-3560) with some modification. Silicone discs (1-cm diameter) are placed into wells of a 24-well plate and incubated overnight at 37° C. with 0.5 mL human plasma (P9523, Sigma-Aldrich Canada). After incubation, the plasma solution is removed and replaced with 1 mL of ~106 CFU mL$^{-1}$ inoculum of the challenge organism in Mueller-Hinton broth II (MHB-II, Oxoid™, Fisher Scientific, ON, Canada). These plates are incubated further for 24 h at 37° C., after which the discs are washed by gentle shaking at 50 rpm for 30 min in 10 mM sterile phosphate buffer saline solution (PBS, pH 7.0, containing 0.85% NaCl) to remove non-adherent cells. After washing, discs are placed in a fresh 24-well plate containing 1 mL PRMSE solution in each well at different concentrations with and without ciprofloxacin (different concentrations) and incubated at 37° C. for 2 h. The discs are then removed and placed in sterile Falcon™ tubes (centrifuge tube 15 mL, Fisher Scientific, ON, Canada) containing 3 mL of 10 mM sterile PBS solution and sonicated in bath sonicator (60 Hz and 150 W) for 10 min to disrupt any remaining biofilm. The bacterial cell concentration in the resulting suspension is quantified using standard plate counts. An independently prepared bacterial suspension is subjected to the same sonication conditions to account for any damage to the cells as a result of this treatment.

Example V

RNA Extraction, cDNA Synthesis, and Comparative qRT-PCR

Bacterial cells are grown to an $OD_{600}$ 0.5-0.8 (16 h, 37° C., 150 rpm) in LB broth with or without different concentrations of PRMSE. Total RNA is extracted using a Direct Zol kit (Zymo Research). RNA concentration is quantified by measuring the absorbance of the sample at 260 and 280 nm, and 300 ng of RNA is used for cDNA synthesis using the high capacity cDNA reverse transcription kit (Applied Biosystems®, Life Technologies Inc., Canada).

Expression of target genes is quantified using quantitative real time PCR (qRT-PCR), using the synthesized cDNA. qRT-PCR is performed with an ABI Prism 7900 HT thermal cycler (Applied Biosystems) using Power SYBR® GREEN PCR master mix (Applied Biosystems®, Life Technologies Inc., Canada). Conditions for qRT-PCR are as follows: 50° C. for 2 min, initial denaturation at 95° C. for 10 min, and 45 cycles of 15 s at 95° C. and 1 min at 60° C. Results are analyzed with SDS software, version 2.2 (Applied Biosystems). Data are normalized to the endogenous reference gene of respective strains. The threshold cycle method ($2^{-\Delta\Delta C_T}$) is used to analyze changes in gene expression in a given sample relative to the control (cells grown under the same conditions without PRMSE). For each sample of cells, qRT-PCR is performed in triplicate and the entire experiment is repeated twice with RNA samples extracted from independent cultures. Oligonucleotide primers are designed (Table 6) using Primer3Plus based on the published genome sequences of CFT073, HI4320, PAO1 and PA14. Moreover, the reported oligonucleotide primers sequences used to amplify the gene of interest are listed in Table 7.

TABLE 7

Primer sequences of the indicated genes used for quantitative RT-PCR.

| | | Oligonucleotide sequence (5'-3') | | | |
|---|---|---|---|---|---|
| Organisms | Genes | Forward | SEQ ID NO: | Reverse | SEQ ID NO: |
| E. coli | gapA* | AAGTTGGTGTTGACGTTGTCGCTG | 1 | ATAACCACTTTCTTCGCACCAGCGG | 2 |
| E. coli | fimA | ACTCTGGCAATCGTTGTTCTGTCG | 3 | ATCAACAGAGCCTGCATCAACTGC | 4 |

TABLE 7-continued

Primer sequences of the indicated genes used for quantitative RT-PCR.

Oligonucleotide sequence (5'-3')

| Organisms | Genes | Forward | SEQ ID NO: | Reverse | SEQ ID NO: |
|---|---|---|---|---|---|
| E. coli | papA2 | ACGGGTGAAATTTGATGGAGCCAC | 5 | AATTCGCAACTGCTGAGAAGGCAC | 6 |
| E. coli | flhD | TCCGCTATGTTTCGTCTCGGCATA | 7 | ACCAGTTGATTGGTTTCTGCCAGC | 8 |
| E. coli | fliC | ACAGCCTCTCGCTGATCACTCAAA | 9 | GCGCTGTTAATACGCAAGCCAGAA | 10 |
| E. coli | acrB | CTGATCATCGTGGTCGGCATGGC | 11 | CCAGTCCTTCAAGGAAACGAACGC | 12 |
| E. coli | motB | GCGTTACGTCCACATCTCAA | 13 | ATGTCGCGCATATAGGGTTC | 14 |
| E. coli | uvrY | GCCAGTTTGTCTGAACGTGA | 15 | CTGTTCACCGTTTTCGGACT | 16 |
| E. coli | marC | GTCGGAAGAGCTGGAAGATG | 17 | GAACTCTGACGCACTGTGGA | 18 |
| E. coli | emrA | ACAGGTAGCGCGTTCTCACT | 19 | AGCGTGGATAAACCGATACG | 20 |
| E. coli | chuA | AGCAAACAACCTGGCTATGG | 21 | CTCTTTATCGAAGGCGTTGC | 22 |
| E. coli | fimH | GGAACCATTCAGGCAGTGAT | 23 | CGGTTTTACAGGCGAATGAC | 24 |
| P. mirabilis | rpoA* | GCAAATCTGGCATTGGCCCTGTTA | 25 | TAGGGCGCTCATCTTCTTCCGAAT | 26 |
| P. mirabilis | MD | AAGGCTTCCGCAATGTTTAGAC | 27 | GTTGCAAATCATCCACTCTGGA | 28 |
| P. mirabilis | flaA | TGCTGGTGCAACTTCATACG | 29 | TTTGTCAGCACCTTCCAGTG | 30 |
| P. mirabilis | ureA | GGGGTGCCAGAGATGATAAA | 31 | CCGGGGATCATGTTATTACC | 32 |
| P. mirabilis | ureD | CCTTACGCACATGCCCTATT | 33 | CTTGTGCAACCGTCAATGTC | 34 |
| P. mirabilis | atfB | ATTTAGCTGCAGCCGACAGT | 35 | GAGTCTGTGCGCCATAATCA | 36 |
| P. mirabilis | marC | ATCTCGGCCACAGTGGTATC | 37 | AATAAAGCGGGGAGATCAGC | 38 |
| P. mirabilis | acrA | GCTGAAATTGCTCGCCTAAC | 39 | GCAACAGCTTGAGCGTACTG | 40 |
| P. mirabilis | cysJ | CAATGCACGTCGTTTAGCTG | 41 | TTCCCCCTGTGTTGAGGTAA | 42 |
| P. aeruginosa | rpoD* | GCCGAGATCAAGGAAATCAA | | GTGTACTTCTTGGCGATGGAA | |
| P. aeruginosa | lasB | AAGCCATCACCGAAGTCAAG | 45 | CGGATCACCAGTTCCACTTT | 46 |
| P. aeruginosa | plcH | TGACTTCGCTGTTCGACTTC | 47 | TGGGCTCGTAGGACCAGTAT | 48 |
| P. aeruginosa | phzS | CGTCGGCATCAATATCCAG | 49 | ATCGAGTACTGCGGATAGGC | 50 |
| P. aeruginosa | pvdA | GTTCCACCACAGCCAGTACC | 51 | CTGTCGTTGAGGTCGATGAA | 52 |
| P. aeruginosa | fliC | AACTTCGACGTAACCGTTGG | 53 | TGGTCAGTACACCCTTGTCG | 54 |
| P. aeruginosa | mexA | CGACCAGGCCGTGAGCAAGCAGC | 55 | GGAGACCTTCGCCGCGTTGTCGC | 56 |
| P. aeruginosa | mexX | TGAAGGCGGCCCTGGACATCAGC | 57 | GATCTGCTCGACGCGGGTCAGCG | 58 |
| P. aeruginosa | oprM | TCAACCTGCGCTACACCA | 59 | GCTACCGTCCTCCAGCTTC | 60 |
| P. aeruginosa | cupA1 | GCGGCAAACACTATCACATTC | 61 | AACAGGGTGGTGAAATGCTC | 62 |
| P. aeruginosa | fleQ | GATCAGCTGACCTGCAACAG | 63 | GCAGGTACTCGTCCCAACTG | 64 |

*Housekeeping genes (Endogenous control)

Example VI

Membrane Permeabilization and Membrane Integrity Assays

The outer membrane permeabilization activities of PRMSE and catechol are determined by the 1-N-phenyl-napthylamine (NPN, Sigma-Aldrich Canada) assay as described in Falla et al., 1996, J. Biol. Chem., 271: 19298-19303) with some modifications. Briefly, overnight bacterial cultures are diluted 1:1 in MHB-II medium to a final volume of 10 mL, with or without sub-MIC supplementation of PRMSE, catechol or gentamycin (positive control), and grown to an $OD_{600}$ of 0.5-0.6 (37° C., 200 rpm). The cells are harvested, washed with 5 mM HEPES buffer (pH 7.2), and resuspended in the same volume (10 mL) of 5 mM HEPES buffer (pH 7.2) containing 1 mM N-ethylmaleimide (NEM, Sigma-Aldrich Canada). Aliquots (1 mL) are mixed with NPN to a final concentration of 10 µM (in cell suspension) and fluorescence is measured using the microplate reader (ex/em 350/420 nm).

The BacLight kit (L-13152, Invitrogen™, Life Technologies Inc., Canada) is used to assess cell membrane damage. Overnight bacterial cultures are diluted 1:40 in fresh MHBII broth to a final volume of 5 mL, grown to an $OD_{600}$ of 0.5-0.6, washed with filter-sterilized 10 mM phosphate buffered saline (PBS, pH 7.0) and resuspended in ⅒ of the original volume. The washed cells are then diluted 1:20 v/v into PRMSE or catechol at 4×MIC or 0.3% v/v DMSO (control). Cultures are incubated at room temperature (21±2° C.) on a tube rocker for 10 min. At the end of the incubation period, an aliquot is taken for CFU counts and the remaining suspension is washed with 10 mM PBS and resuspended to an $OD_{600}$ of 0.3. An aliquot (100 µL) of each bacterial suspension is removed and added to a 96-well, black, clear-bottom plate (Corning™, Fisher Scientific, ON, Canada) along with an equal volume of the BacLight™ reagent (2× stock solution, L13152, Invitrogen™, Life Technologies Inc., Canada) and the plates are incubated for 10 min at room temperature in the dark. At the end of the incubation period, fluorescence intensity is recorded for both kit components, SYTO-9 (ex/em 485/530 nm) and propidium iodide (ex/em 485/645 nm), using the microplate reader. Fluorescence readings from samples are normalized to the values obtained from untreated control to determine the ratio of membrane compromised cells to cells with intact membrane. Cetyltrimethylammonium bromide (CTAB, Sigma-Aldrich Canada), a cationic detergent that is known to cause membrane damage, is used at concentration of 10 µM as a positive control for membrane disruption.

Example VII

Ethidium Bromide (EtBr) Efflux Assay

To assess the effect of PRMSE and catechol on the inhibition of the proton motive force-driven multidrug efflux pump, an ethidium bromide (EtBr) efflux assay was performed using the method described in Kaatz et al. (2000, Antimicrob. Agents Chemother., 44: 1404-1406). An overnight grown culture of each strain is diluted 1:100 using MHB-II broth to a final volume of 10 mL and grown to an $OD_{600}$ of 0.8-1.0 (at 37° C., 150 rpm). Cells are loaded in polystyrene microcentrifuge tubes (2 mL) and mixed with 5 µM EtBr and PRMSE or catechol at 25% of their MIC, or 100 µM of the proton conductor, carbonyl cyanide m-chlorophenylhydrazone (CCCP, Sigma-Aldrich Canada), as positive control. Replica tubes that do not receive PRMSE, catechol or proton conductor served as negative controls. The tubes are incubated for 1 h (37° C., 150 rpm). The inoculum is then adjusted to 0.4 OD600 with MHB-II broth containing 5 µM EtBr and 2 mL aliquots of this mixture are pelleted (5000×g, 10 min at 4° C.). The pellets are incubated on ice immediately, resuspended in 1 mL of MHB-II, and aliquoted (200 µL) into a polystyrene 96 well black, clear-bottom plate (Corning™, Fisher Scientific, ON, Canada). EtBr efflux from the cells is monitored at room temperature using the microplate reader (ex/em 530/600 nm). Readings are taken at 5 min intervals for 1 h to monitor efflux pump activity. The background fluorescence of the medium is subtracted from all measurements and the assay is repeated independently in triplicate.

Example VIII

Galleria mellonella Larvae (Wax Moth) Infection Assay

G. mellonella infection assay is performed as described previously with some modification (Jander et al., 2000, J Bacteriol., 182: 3843-3845). Briefly, PA14 culture grown overnight in TSB broth is diluted 1:100 in the same growth medium and further grown to $OD_{600}$ nm of 1.27 at 37° C. under 100 rpm shaking. Freshly grown culture is centrifuged, and pellets are washed and resuspended in 10 mM $MgSO_4$ to an OD600 of 0.1. To prepare the lethal dose of P. aeruginosa PA14 culture serial 10-fold dilutions are made in 10 mM $MgSO_4$ supplemented with 1 mg/mL of ampicillin (adjusted to about $1-10^3$ bacterial cells in 5 µL of suspension) containing or not containing PRMSE, without and with ciprofloxacin at sub-MICs. Ampicillin is used to prevent infection by bacterial contaminants on the surface of the larvae at a final concentration of approximately 5 ng per larva during survival phase. G. mellonella larvae are injected with 5 µL aliquot of each treatment solution using pre-washed Hamilton syringe. Five larvae are injected per each treatment and the assay is performed in triplicate. PRMSE and ciprofloxacin at sub-MICs are assessed individually to monitor adverse effect on larvae survival. To analyze the effect of PRMSE on G. mellonella survival post-PA14 infection, an additional set of larvae are first injected with bacteria at their proleg, and after 2 h they are injected at second proleg with 5 µL saline solution containing or not PRMSE without and with ciprofloxacin (at selected concentrations in ng per larva). All injected larvae are incubated in Petri plates at 28° C. under the dark condition, and the number of dead larvae is scored daily after infection. A larva is considered dead when it displays no vital signs in response to touch. A mock inoculation using prewashed Hamilton syringe is also performed in each experiment to monitor the killing due to physical injury or infection by pathogenic contaminants. To rule out any growth-inhibitory effect of PRMSE on PA14 cells due to induction of the immune response, production of antimicrobial peptides or transformation of the extract into a toxic compound(s) in the larval hemolymph, an additional set of larvae are injected with 5 µL of PRMSE without and with ciprofloxacin (sub-MICs) or saline solution as a control. The larval hemolymph is recovered at 3 h after the treatment and 5 µL aliquot of each larval hemolymph sample is spotted on the Pseudomonas isolation agar (BD-Difco) plates previously inoculated with PA14 cells to produce a lawn of confluent growth. The appearance of growth inhibition halos is verified after 24 h of incubation at 37° C.

Example IX

Drosophila melanogaster (Fruit Fly) Infection Assay

In this infection assay, PRMSE was analyzed for its anti-infective activity. As well, antibiotic ciprofloxacin is analyzed in combination with PRMSE for its synergistic anti-infective interactions. Fruit flies (*D. melanogaster*) are infected orally in fly feeding assay as before (Lutter et al., 2008, Infect Immun., 76: 1877-1888), with some modifications. Briefly, flies are anesthetized under a gentle stream of carbon dioxide. Male flies (3- to 5-days-old) are starved of food and water for 5-6 h and separated into vials (10 per vial) containing 5 ml of 5% sucrose agar (sterile) without and with phenolic extract without and with antibiotic at sub-MICs and 2.3-cm filter paper disks (sterile) containing freshly grown bacterial culture suspension. To achieve this freshly grown culture, an overnight *P. aeruginosa* PA14 culture is inoculated in 6 mL TSB culture and incubated at 37° C. and 100 rpm until $OD_{600}$=3.0. This culture is centrifuged at 12,000×g for 1 min and the resulting pellet resuspended in 150 μL of sterile 5% sucrose, without and with sub-MICs of phenolic extract or antibiotic. All filters are soaked appropriately with 150 μL of culture suspension prepared in sterile 5% sucrose without and with sub-MICs of PRMSE or antibiotic, and placed over 5% sucrose agar using sterile forceps, in each feeding vial prior to transferring flies into the vial. Separate feeding vials with soaked filter disks with 150 μL of 5% sucrose without PA14 cells, PRMSE or antibiotic, on 5% sucrose agar are used as negative controls for each experiment. Post-infection mortality of flies is monitored daily for 14 days, with each treatment tested twice in duplicate.

The difference in the treated or untreated PA14 strains' ability to kill *D. melanogaster* in this feeding assay may have been due to modified survival of the bacteria on the filter papers used for exposure during incubation. To address this possibility, the survival of PA14 on the paper discs without and with sub-MICs of PRMSE or antibiotic under the same conditions as the fly feeding assay is analyzed.

Enumeration of viable bacteria on filters during the infection period is performed using separate test vials with different treatments inoculated with *P. aeruginosa* PA14 and inoculated control sucrose vials that are sampled on alternative days, up to 6 days during infection period. Briefly, filters from the test vials are removed in a sterile environment, placed in 50 mL polypropylene tube containing 5 mL of LB broth and vortexed for 30 s. This LB medium containing the sampled bacterial cells is serially diluted in phosphate buffer saline solution (pH 7.4), and 30 μL is plated onto *Pseudomonas* isolation agar (BD-Difco). Colonies are enumerated after the incubation at 37° C. for 24 h.

Example X

Enzyme Inhibition Assays

The filter-sterilized culture supernatant samples are prepared from late stationary phase cultures of *P. aeruginosa* PAO1 and PA14 grown without and with PRMSE at different concentrations. For assessment of LasA staphylolytic activity, 5 mL of *Staphylococcus aureus* ATCC 25923 overnight cultures are boiled for 15 min, and 100 μL are mixed with 300 μL of filtered culture supernatants of PAO1 and PA14. The $OD_{600}$ is measured after 2 h of incubation at 37° C. and 100 rpm. To analyze alkaline protease (AprA) activity, filter-sterilized culture supernatant samples (200 μL) of PAO1 and PA14 are vortexed with 25 mg of Hide-Remazol Brilliant Blue R powder (Sigma-Aldrich) in 800 μL of 20 mM Tris-HCl buffer (pH 8.0) containing 1 mM $CaCl_2$. The tube is then incubated at 37° C. at 150 rpm for 1 h. The insoluble hide azure blue is removed by centrifugation at 10,000×g for 4 min at 4° C. and the absorption of the supernatant is measured at 595 nm. All enzyme assay experiments are carried out in triplicate. Total proteolytic activity is assessed using LB agar plates containing 2% (w/v) skim milk powder.

While the present disclosure has been described in connection with specific embodiments thereof, it will be understood that it is capable of further modifications and this application is intended to cover any variations, uses, or adaptations, including such departures from the present disclosure as come within known or customary practice within the art and as may be applied to the essential features hereinbefore set forth, and as follows in the scope of the appended claims.

---

What is claimed is:

1. An anti-microbial composition with synergistic effect comprising a phenolic-rich maple syrup extract and at least one antibiotic.

2. The composition of claim 1, wherein the at least one antibiotic is a fluoroquinolone antibiotic, a β-lactam antibiotic, aminoglycoside, polyketides, glycopeptides, benzenoids, macrolides, ansamycins, sulfonamides, chloramphenicol, oxazolidinones, carboxylic acids antibiotic, organic phosphonic acids antibiotic, quinolones and their derivatives.

3. The composition of claim 1, wherein the at least one antibiotic is at least one of ciprofloxacin, carbenicillin, ampicillin, penicillin, kanamycin, gentamycin, tetracycline, levofloxacin, trimethoprim, sulfamethoxazole, norfloxacin, nitrofurantoin, fosfomycin, azithromycin, minocycline, amikacin, cephalosporin, erythromycin, daptomycin, vancomycin and their derivatives.

4. The composition of claim 1, wherein the phenolic-rich maple syrup extract is from *Acer nigrum, Acer lanum, Acer acuminatum, Acer albopurpurascens, Acer argutum, Acer barbinerve, Acer buergerianum, Acer caesium, Acer campbellii, Acer campestre, Acer capillipes, Acer cappadocicum, Acer carpinifolium, Acer caudatifolium, Acer caudatum, Acer cinnamomifolium, Acer circinaturn, Acer cissifolium, Acer crassum, Acer crataegifolium, Acer davidii, Acer decandrum, Acer diabolicum, Acer distylum, Acer divergens, Acer erianthum, Acer erythranthum, Acer fabri, Acer garrettii, Acer glabrum, Acer grandidentatum, Acer griseum, Acer heldreichii, Acer henryi, Acer hyrcanum, Acer ibericum, Acer japonicum, Acer kungshanense, Acer kweilinense, Acer laevigatum, Acer laurinum, Acer lobelii, Acer lucidum, Acer macrophyllum, Acer mandshuricum, Acer maximowiczianum, Acer miaoshanicum, Acer micranthum, Acer miyabei, Acer mono, Acer monox, Acer truncatum, Acer monspessulanum, Acer negundo, Acer ningpoense, Acer nipponicum, Acer oblongum, Acer obtusifolium, Acer oliverianum, Acer opalus, Acer palmatum, Acer paxii, Acer pectinatum, Acer pensylvanicum, Acer pentaphyllum, Acer pentapomicum, Acer pictum, Acer pilosum, Acer platanoides, Acer poliophyllum, Acer pseudoplatanus, Acer pseudosieboldianum, Acer pubinerve, Acer pycnanthum, Acer rubrum, Acer rufinerve, Acer saccharinum, Acer saccharum, Acer sempervirens, Acer shirasawanum, Acer sieboldianum, Acer sinopurpurescens, Acer spicatum, Acer stachyophyllum, Acer sterculiaceum, Acer takesimense, Acer tataricum, Acer tegmentosum, Acer tenuifolium, Acer tetramerum, Acer trautvetteri, Acer triflorum, Acer truncatum, Acer tschonoskii, Acer turcomanicum, Acer ukurunduense, Acer velutinum, Acer wardii, Acer×peronai*, or *Acer×pseudoheldreichii*.

5. The composition of claim 1, wherein said composition reduces biofilm formation of a bacterial strain.

6. The composition of claim 1, wherein the anti-microbial composition is against Gram-negative or Gram-positive bacteria.

7. The composition of claim 1, wherein the anti-microbial composition is against a bacterial strain of *Escherichia coli, Proteus mirabilis, Pseudomonas aeruginosa, Salmonella* species, *Enterobacter cloacae, Burkholderia cepacia, Chromobacterium violaceum, Klebsiella pneumoniae, Helicobacter pylori, Acinetobacter baumannii, Vibrio cholera, Mycoplasma pneumoniae, Neisseria gonorrhoeae, Legionella pneumophila, Serratia* species, *Shigella* species, *Rickettsia rickettsia, Chlamydia pneumoniae, Mycobacterium tuberculosis, Yersinia* species, *Moraxella catarrhalis* or *Proteobacteria* pathogens.

8. The composition of claim 1, wherein the extract comprises a catechol, a catechaldehyde, a gallic acid, a syringaldehyde, a vanillin, and/or a hydroxybenzoic acid.

9. The composition of claim 1, wherein said composition represses the expression of a gene associated with multiple drug resistance, motility, virulence determinants, adhesion and/or biofilm formation.

10. The composition of claim 9, wherein said gene associated with multiple drug resistance is emrA, acre, marC, acrA, oprM, mexA or mexX.

11. The composition of claim 9, wherein said gene associated with motility is fliC, flhD, motB, fimH, fimA, papA2, flaA, fleQ.

12. The composition of claim 9, wherein said gene associated with virulence determinants is chuA, cysJ, plcH, phzS or pvdA.

13. The composition of claim 9, wherein said gene associated with adhesion is fimH, fimA, papA2, atfB, cupA1 or pelA.

14. The composition of claim 9, wherein said gene associated with biofilm formation is uvrY, ureD or lasB.

15. A method of treating a bacterial infection comprising administering to a subject in need thereof the anti-microbial composition of claim 1.

* * * * *

UNITED STATES PATENT AND TRADEMARK OFFICE
CERTIFICATE OF CORRECTION

PATENT NO. : 10,206,906 B2
APPLICATION NO. : 15/159980
DATED : February 19, 2019
INVENTOR(S) : Nathalie Tufenkji and Vimal Maisuria Page 1 of 1

It is certified that error appears in the above-identified patent and that said Letters Patent is hereby corrected as shown below:

In the Specification

At Column 18 Lines 14-36 should read:
The relative level of phenolic compounds in PRMSE is estimated using HPLC, as reported in the literature (Sadiki and Martin, 2013, Food Anal. Methods, 6:737-744). Samples are analyzed using Agilent Technologies 1200 Series analytical liquid chromatographic system, consisting of a quaternary pumps G1311A, degasser G1322A, column oven G1316A, auto sampler G1329A and UV detector G1315D. Phenolic compounds are separated on a Zorbax Eclipse XDB-C18 column (4.6×150 mm, 5um; Agilent) at 30° C. Trifluoroacetic acid at 0.2% (phase A) and methanol (phase B) are used as eluents. The elution gradient starts with 2% phase B, increased to 40% phase B at 40 min, 80% phase B at 50 min, and held at 80% for 2 min. The injection volume is 10 uL and the flow rate is 0.5 mL min'. Data are collected and evaluated by the ChemStation Software. The analytes are identified by comparing retention times and UV spectra, recorded in the range of 200-400 nm, with the individual chromatogram of each phenolic standard. The following pure phenolic compounds were used as standards: gallic acid, 1,2-dihydroxybenzene (catechol), 3,4-dihydroxybenzaldehyde (catechaldehyde), Syringaldehyde, vanillin and 3-hydroxybenzoic acid.

Signed and Sealed this
Twenty-eighth Day of July, 2020

Andrei Iancu
*Director of the United States Patent and Trademark Office*

SEQUENCE LISTING

<160> NUMBER OF SEQ ID NOS: 64

<210> SEQ ID NO 1
<211> LENGTH: 24
<212> TYPE: DNA
<213> ORGANISM: Artificial Sequence
<220> FEATURE:
<223> OTHER INFORMATION: Forward primer gapA

<400> SEQUENCE: 1
aagttggtgt tgacgttgtc gctg           24

<210> SEQ ID NO 2
<211> LENGTH: 25
<212> TYPE: DNA
<213> ORGANISM: Artificial Sequence
<220> FEATURE:
<223> OTHER INFORMATION: Reverse primer gapA

```
<400> SEQUENCE: 2
ataaccactt tcttcgcacc agcgg                                    25

<210> SEQ ID NO 3
<211> LENGTH: 24
<212> TYPE: DNA
<213> ORGANISM: Artificial Sequence
<220> FEATURE:
<223> OTHER INFORMATION: Forward primer filmA

<400> SEQUENCE: 3
actctggcaa tcgttgttct gtcg                                     24

<210> SEQ ID NO 4
<211> LENGTH: 24
<212> TYPE: DNA
<213> ORGANISM: Artificial Sequence
<220> FEATURE:
<223> OTHER INFORMATION: Reverse primer firmA

<400> SEQUENCE: 4
atcaacagag cctgcatcaa ctgc                                     24

<210> SEQ ID NO 5
<211> LENGTH: 24
<212> TYPE: DNA
<213> ORGANISM: Artificial Sequence
<220> FEATURE:
<223> OTHER INFORMATION: Forward primer papA2

<400> SEQUENCE: 5
acgggtgaaa tttgatggag ccac                                     24

<210> SEQ ID NO 6
<211> LENGTH: 24
<212> TYPE: DNA
<213> ORGANISM: Artificial Sequence
<220> FEATURE:
<223> OTHER INFORMATION: Reverse primer papA2

<400> SEQUENCE: 6
aattcgcaac tgctgagaag gcac                                     24

<210> SEQ ID NO 7
<211> LENGTH: 24
<212> TYPE: DNA
<213> ORGANISM: Artificial Sequence
<220> FEATURE:
<223> OTHER INFORMATION: Forward primer flhD

<400> SEQUENCE: 7
tccgctatgt ttcgtctcgg cata                                     24

<210> SEQ ID NO 8
<211> LENGTH: 24
<212> TYPE: DNA
<213> ORGANISM: Artificial Sequence
<220> FEATURE:
<223> OTHER INFORMATION: Reverse primer flhD

<400> SEQUENCE: 8
accagttgat tggtttctgc cagc                                     24
```

```
<210> SEQ ID NO 9
<211> LENGTH: 24
<212> TYPE: DNA
<213> ORGANISM: Artificial Sequence
<220> FEATURE:
<223> OTHER INFORMATION: Forward primer fliC

<400> SEQUENCE: 9
acagcctctc gctgatcact caaa                                              24

<210> SEQ ID NO 10
<211> LENGTH: 24
<212> TYPE: DNA
<213> ORGANISM: Artificial Sequence
<220> FEATURE:
<223> OTHER INFORMATION: Reverse primer fliC

<400> SEQUENCE: 10
gcgctgttaa tacgcaagcc agaa                                              24

<210> SEQ ID NO 11
<211> LENGTH: 23
<212> TYPE: DNA
<213> ORGANISM: Artificial Sequence
<220> FEATURE:
<223> OTHER INFORMATION: Forward primer acrB

<400> SEQUENCE: 11
ctgatcatcg tggtcggcat ggc                                               23

<210> SEQ ID NO 12
<211> LENGTH: 24
<212> TYPE: DNA
<213> ORGANISM: Artificial Sequence
<220> FEATURE:
<223> OTHER INFORMATION: Reverse primer acrB

<400> SEQUENCE: 12
ccagtccttc aaggaaacga acgc                                              24

<210> SEQ ID NO 13
<211> LENGTH: 20
<212> TYPE: DNA
<213> ORGANISM: Artificial Sequence
<220> FEATURE:
<223> OTHER INFORMATION: Forward primer motB

<400> SEQUENCE: 13
gcgttacgtc cacatctcaa                                                   20

<210> SEQ ID NO 14
<211> LENGTH: 20
<212> TYPE: DNA
<213> ORGANISM: Artificial Sequence
<220> FEATURE:
<223> OTHER INFORMATION: Reverse primer motB

<400> SEQUENCE: 14
atgtcgcgca tatagggttc                                                   20

<210> SEQ ID NO 15
<211> LENGTH: 20
<212> TYPE: DNA
<213> ORGANISM: Artificial Sequence
<220> FEATURE:
<223> OTHER INFORMATION: Forward primer uvrY
```

```
<400> SEQUENCE: 15
gccagtttgt ctgaacgtga                                             20

<210> SEQ ID NO 16
<211> LENGTH: 20
<212> TYPE: DNA
<213> ORGANISM: Artificial Sequence
<220> FEATURE:
<223> OTHER INFORMATION: Reverse primer uvrY

<400> SEQUENCE: 16
ctgttcaccg ttttcggact                                             20

<210> SEQ ID NO 17
<211> LENGTH: 20
<212> TYPE: DNA
<213> ORGANISM: Artificial Sequence
<220> FEATURE:
<223> OTHER INFORMATION: Forward primer marC

<400> SEQUENCE: 17
gtcggaagag ctggaagatg                                             20

<210> SEQ ID NO 18
<211> LENGTH: 20
<212> TYPE: DNA
<213> ORGANISM: Artificial Sequence
<220> FEATURE:
<223> OTHER INFORMATION: Reverse primer marC

<400> SEQUENCE: 18
gaactctgac gcactgtgga                                             20

<210> SEQ ID NO 19
<211> LENGTH: 20
<212> TYPE: DNA
<213> ORGANISM: Artificial Sequence
<220> FEATURE:
<223> OTHER INFORMATION: Forward primer emrA

<400> SEQUENCE: 19
acaggtagcg cgttctcact                                             20

<210> SEQ ID NO 20
<211> LENGTH: 20
<212> TYPE: DNA
<213> ORGANISM: Artificial Sequence
<220> FEATURE:
<223> OTHER INFORMATION: Reverse primer emrA

<400> SEQUENCE: 20
agcgtggata aaccgatacg                                             20

<210> SEQ ID NO 21
<211> LENGTH: 20
<212> TYPE: DNA
<213> ORGANISM: Artificial Sequence
<220> FEATURE:
<223> OTHER INFORMATION: Forward primer chuA

<400> SEQUENCE: 21
agcaaacaac ctggctatgg                                             20
```

<210> SEQ ID NO 22
<211> LENGTH: 20
<212> TYPE: DNA
<213> ORGANISM: Artificial Sequence
<220> FEATURE:
<223> OTHER INFORMATION: Reverse primer chuA

<400> SEQUENCE: 22
ctctttatcg aaggcgttgc                                              20

<210> SEQ ID NO 23
<211> LENGTH: 20
<212> TYPE: DNA
<213> ORGANISM: Artificial Sequence
<220> FEATURE:
<223> OTHER INFORMATION: Forward primer fimH

<400> SEQUENCE: 23
ggaaccattc aggcagtgat                                              20

<210> SEQ ID NO 24
<211> LENGTH: 20
<212> TYPE: DNA
<213> ORGANISM: Artificial Sequence
<220> FEATURE:
<223> OTHER INFORMATION: Reverse primer fimH

<400> SEQUENCE: 24
cggttttaca ggcgaatgac                                              20

<210> SEQ ID NO 25
<211> LENGTH: 24
<212> TYPE: DNA
<213> ORGANISM: Artificial Sequence
<220> FEATURE:
<223> OTHER INFORMATION: Forward primer rpoA

<400> SEQUENCE: 25
gcaaatctgg cattggccct gtta                                         24

<210> SEQ ID NO 26
<211> LENGTH: 24
<212> TYPE: DNA
<213> ORGANISM: Artificial Sequence
<220> FEATURE:
<223> OTHER INFORMATION: Reverse primer rpoA

<400> SEQUENCE: 26
tagggcgctc atcttcttcc gaat                                         24

<210> SEQ ID NO 27
<211> LENGTH: 22
<212> TYPE: DNA
<213> ORGANISM: Artificial Sequence
<220> FEATURE:
<223> OTHER INFORMATION: Forward primer flhD

<400> SEQUENCE: 27
aaggcttccg caatgtttag ac                                           22

<210> SEQ ID NO 28
<211> LENGTH: 22
<212> TYPE: DNA
<213> ORGANISM: Artificial Sequence
<220> FEATURE:
<223> OTHER INFORMATION: Reverse primer flhD

```
<400> SEQUENCE: 28
gttgcaaatc atccactctg ga                                          22

<210> SEQ ID NO 29
<211> LENGTH: 20
<212> TYPE: DNA
<213> ORGANISM: Artificial Sequence
<220> FEATURE:
<223> OTHER INFORMATION: Forward primer flaA

<400> SEQUENCE: 29
tgctggtgca acttcatacg                                             20

<210> SEQ ID NO 30
<211> LENGTH: 20
<212> TYPE: DNA
<213> ORGANISM: Artificial Sequence
<220> FEATURE:
<223> OTHER INFORMATION: Reverse primer flaA

<400> SEQUENCE: 30
tttgtcagca ccttccagtg                                             20

<210> SEQ ID NO 31
<211> LENGTH: 20
<212> TYPE: DNA
<213> ORGANISM: Artificial Sequence
<220> FEATURE:
<223> OTHER INFORMATION: Forward primer ureA

<400> SEQUENCE: 31
ggggtgccag agatgataaa                                             20

<210> SEQ ID NO 32
<211> LENGTH: 20
<212> TYPE: DNA
<213> ORGANISM: Artificial Sequence
<220> FEATURE:
<223> OTHER INFORMATION: Reverse primer ureA

<400> SEQUENCE: 32
ccggggatca tgttattacc                                             20

<210> SEQ ID NO 33
<211> LENGTH: 20
<212> TYPE: DNA
<213> ORGANISM: Artificial Sequence
<220> FEATURE:
<223> OTHER INFORMATION: Forward primer ureD

<400> SEQUENCE: 33
ccttacgcac atgccctatt                                             20

<210> SEQ ID NO 34
<211> LENGTH: 20
<212> TYPE: DNA
<213> ORGANISM: Artificial Sequence
<220> FEATURE:
<223> OTHER INFORMATION: Reverse primer ureD

<400> SEQUENCE: 34
cttgtgcaac cgtcaatgtc                                             20
```

```
<210> SEQ ID NO 35
<211> LENGTH: 20
<212> TYPE: DNA
<213> ORGANISM: Artificial Sequence
<220> FEATURE:
<223> OTHER INFORMATION: Forward primer atfB

<400> SEQUENCE: 35
atttagctgc agccgacagt                                            20

<210> SEQ ID NO 36
<211> LENGTH: 20
<212> TYPE: DNA
<213> ORGANISM: Artificial Sequence
<220> FEATURE:
<223> OTHER INFORMATION: Reverse primer atfB

<400> SEQUENCE: 36
gagtctgtgc gccataatca                                            20

<210> SEQ ID NO 37
<211> LENGTH: 20
<212> TYPE: DNA
<213> ORGANISM: Artificial Sequence
<220> FEATURE:
<223> OTHER INFORMATION: Forward primer marC

<400> SEQUENCE: 37
atctcggcca cagtggtatc                                            20

<210> SEQ ID NO 38
<211> LENGTH: 20
<212> TYPE: DNA
<213> ORGANISM: Artificial Sequence
<220> FEATURE:
<223> OTHER INFORMATION: Reverse primer marC

<400> SEQUENCE: 38
aataaagcgg ggagatcagc                                            20

<210> SEQ ID NO 39
<211> LENGTH: 20
<212> TYPE: DNA
<213> ORGANISM: Artificial Sequence
<220> FEATURE:
<223> OTHER INFORMATION: Forward primer acrA

<400> SEQUENCE: 39
gctgaaattg ctcgcctaac                                            20

<210> SEQ ID NO 40
<211> LENGTH: 20
<212> TYPE: DNA
<213> ORGANISM: Artificial Sequence
<220> FEATURE:
<223> OTHER INFORMATION: Reverse primer acrA

<400> SEQUENCE: 40
gcaacagctt gagcgtactg                                            20

<210> SEQ ID NO 41
<211> LENGTH: 20
<212> TYPE: DNA
<213> ORGANISM: Artificial Sequence
<220> FEATURE:
<223> OTHER INFORMATION: Forward primer cysJ
```

```
<400> SEQUENCE: 41
caatgcacgt cgtttagctg                                          20

<210> SEQ ID NO 42
<211> LENGTH: 20
<212> TYPE: DNA
<213> ORGANISM: Artificial Sequence
<220> FEATURE:
<223> OTHER INFORMATION: Reverse primer cysJ

<400> SEQUENCE: 42
ttccccctgt gttgaggtaa                                          20

<210> SEQ ID NO 43
<211> LENGTH: 20
<212> TYPE: DNA
<213> ORGANISM: Artificial Sequence
<220> FEATURE:
<223> OTHER INFORMATION: Forward primer rpoD

<400> SEQUENCE: 43
gccgagatca aggaaatcaa                                          20

<210> SEQ ID NO 44
<211> LENGTH: 21
<212> TYPE: DNA
<213> ORGANISM: Artificial Sequence
<220> FEATURE:
<223> OTHER INFORMATION: Reverse primer rpoD

<400> SEQUENCE: 44
gtgtacttct tggcgatgga a                                        21

<210> SEQ ID NO 45
<211> LENGTH: 20
<212> TYPE: DNA
<213> ORGANISM: Artificial Sequence
<220> FEATURE:
<223> OTHER INFORMATION: Forward primer lasB

<400> SEQUENCE: 45
aagccatcac cgaagtcaag                                          20

<210> SEQ ID NO 46
<211> LENGTH: 20
<212> TYPE: DNA
<213> ORGANISM: Artificial Sequence
<220> FEATURE:
<223> OTHER INFORMATION: Reverse primer lasB

<400> SEQUENCE: 46
cggatcacca gttccacttt                                          20

<210> SEQ ID NO 47
<211> LENGTH: 20
<212> TYPE: DNA
<213> ORGANISM: Artificial Sequence
<220> FEATURE:
<223> OTHER INFORMATION: Forward primer plcH

<400> SEQUENCE: 47
tgacttcgct gttcgacttc                                          20
```

<210> SEQ ID NO 48
<211> LENGTH: 20
<212> TYPE: DNA
<213> ORGANISM: Artificial Sequence
<220> FEATURE:
<223> OTHER INFORMATION: Reverse primer plcH

<400> SEQUENCE: 48
tgggctcgta ggaccagtat                                          20

<210> SEQ ID NO 49
<211> LENGTH: 19
<212> TYPE: DNA
<213> ORGANISM: Artificial Sequence
<220> FEATURE:
<223> OTHER INFORMATION: Forward primer phzS

<400> SEQUENCE: 49
cgtcggcatc aatatccag                                           19

<210> SEQ ID NO 50
<211> LENGTH: 20
<212> TYPE: DNA
<213> ORGANISM: Artificial Sequence
<220> FEATURE:
<223> OTHER INFORMATION: Reverse primer phzS

<400> SEQUENCE: 50
atcgagtact gcggataggc                                          20

<210> SEQ ID NO 51
<211> LENGTH: 20
<212> TYPE: DNA
<213> ORGANISM: Artificial Sequence
<220> FEATURE:
<223> OTHER INFORMATION: Forward primer pvdA

<400> SEQUENCE: 51
gttccaccac agccagtacc                                          20

<210> SEQ ID NO 52
<211> LENGTH: 20
<212> TYPE: DNA
<213> ORGANISM: Artificial Sequence
<220> FEATURE:
<223> OTHER INFORMATION: Reverse primer pvdA

<400> SEQUENCE: 52
ctgtcgttga ggtcgatgaa                                          20

<210> SEQ ID NO 53
<211> LENGTH: 20
<212> TYPE: DNA
<213> ORGANISM: Artificial Sequence
<220> FEATURE:
<223> OTHER INFORMATION: Forward primer fliC

<400> SEQUENCE: 53
aacttcgacg taaccgttgg                                          20

<210> SEQ ID NO 54
<211> LENGTH: 20
<212> TYPE: DNA
<213> ORGANISM: Artificial Sequence
<220> FEATURE:
<223> OTHER INFORMATION: Reverse primer fliC

<400> SEQUENCE: 54
tggtcagtac acccttgtcg                                           20

<210> SEQ ID NO 55
<211> LENGTH: 23
<212> TYPE: DNA
<213> ORGANISM: Artificial Sequence
<220> FEATURE:
<223> OTHER INFORMATION: Forward primer mexA

<400> SEQUENCE: 55
cgaccaggcc gtgagcaagc agc                                       23

<210> SEQ ID NO 56
<211> LENGTH: 23
<212> TYPE: DNA
<213> ORGANISM: Artificial Sequence
<220> FEATURE:
<223> OTHER INFORMATION: Reverse primer mexA

<400> SEQUENCE: 56
ggagaccttc gccgcgttgt cgc                                       23

<210> SEQ ID NO 57
<211> LENGTH: 23
<212> TYPE: DNA
<213> ORGANISM: Artificial Sequence
<220> FEATURE:
<223> OTHER INFORMATION: Forward primer mexX

<400> SEQUENCE: 57
tgaaggcggc cctggacatc agc                                       23

<210> SEQ ID NO 58
<211> LENGTH: 23
<212> TYPE: DNA
<213> ORGANISM: Artificial Sequence
<220> FEATURE:
<223> OTHER INFORMATION: Reverse primer mexX

<400> SEQUENCE: 58
gatctgctcg acgcgggtca gcg                                       23

<210> SEQ ID NO 59
<211> LENGTH: 18
<212> TYPE: DNA
<213> ORGANISM: Artificial Sequence
<220> FEATURE:
<223> OTHER INFORMATION: Forward primer oprM

<400> SEQUENCE: 59
tcaacctgcg ctacacca                                             18

<210> SEQ ID NO 60
<211> LENGTH: 19
<212> TYPE: DNA
<213> ORGANISM: Artificial Sequence
<220> FEATURE:
<223> OTHER INFORMATION: Reverse primer oprM

<400> SEQUENCE: 60
gctaccgtcc tccagcttc                                            19

```
<210> SEQ ID NO 61
<211> LENGTH: 21
<212> TYPE: DNA
<213> ORGANISM: Artificial Sequence
<220> FEATURE:
<223> OTHER INFORMATION: Forward primer cupA1

<400> SEQUENCE: 61
gcggcaaaca ctatcacatt c                                          21

<210> SEQ ID NO 62
<211> LENGTH: 20
<212> TYPE: DNA
<213> ORGANISM: Artificial Sequence
<220> FEATURE:
<223> OTHER INFORMATION: Reverse primer cupA1

<400> SEQUENCE: 62
aacagggtgg tgaaatgctc                                            20

<210> SEQ ID NO 63
<211> LENGTH: 20
<212> TYPE: DNA
<213> ORGANISM: Artificial Sequence
<220> FEATURE:
<223> OTHER INFORMATION: Forward primer fleQ

<400> SEQUENCE: 63
gatcagctga cctgcaacag                                            20

<210> SEQ ID NO 64
<211> LENGTH: 20
<212> TYPE: DNA
<213> ORGANISM: Artificial Sequence
<220> FEATURE:
<223> OTHER INFORMATION: Reverse primer fleQ

<400> SEQUENCE: 64
gcaggtactc gtcccaactg                                            20
```